US005686579A

United States Patent [19]
Shami et al.

[11] Patent Number: 5,686,579
[45] Date of Patent: Nov. 11, 1997

[54] USE OF ANTIBODY/ANTIGEN INTERACTIONS TO PROTECT BIOLOGICALLY ACTIVE PROTEINS AND PEPTIDES

[75] Inventors: Ezekiel Y. Shami; Aser Rothstein; Mohabir Ramjeesingh, all of Ontario, Canada

[73] Assignee: Hybrisens, Ltd., Toronto, Canada

[21] Appl. No.: 447,422

[22] Filed: May 23, 1995

Related U.S. Application Data

[63] Continuation of Ser. No. 81,410, Jun. 22, 1993, abandoned, which is a continuation-in-part of Ser. No. 938,505, Aug. 31, 1992, abandoned, which is a continuation of Ser. No. 205,748, Jun. 21, 1988, abandoned.

[51] Int. Cl.$^6$ .................. C07K 19/00; C07H 21/04
[52] U.S. Cl. .................. 530/387.3; 536/23.4; 435/172.1; 435/71.1; 435/240.27; 435/183
[58] Field of Search .................. 530/387.3; 536/23.4; 435/172.1, 71.1, 240.27, 183

[56] References Cited

U.S. PATENT DOCUMENTS

| 4,059,685 | 11/1977 | Johnson et al. | 424/12 |
| 4,179,337 | 12/1979 | Davis et al. | 435/181 |
| 4,704,692 | 11/1987 | Ladner | 364/496 |

FOREIGN PATENT DOCUMENTS

| 0 172 153 | 2/1986 | European Pat. Off. |
| 0 231 649 | 8/1987 | European Pat. Off. |
| 0 287 187 | 10/1988 | European Pat. Off. |
| 0 298 654 | 1/1989 | European Pat. Off. |
| WO 85/00974 | 8/1984 | WIPO |

OTHER PUBLICATIONS

M. G. Rosenblum et al., "Modification of Human Leukocyte Interferon Pharmacology with a Monoclonal Antibody", *Cancer Research*, 45: 2421–2424 (Jun. 1985).
G. T. Davis et al., "Single Chain Antibody (SCA) Encoding Genes: One–Step Construction and Expression in Eukarytic Cells", *Bio/Technology*, 9: 165–169 (Feb. 1991).
M. Ramjeesingh, et al., "Monoclonal Antibodies Can Protect$_L$–Asparaginase Against Inactivation by Trypsin", *Bio/Technology*, 10: 442–445 (Apr. 1992).
N. Zyk, "Modification of $_L$–Asparaginase EC–$_2$ by Honologous Antibodies", *Biochimica et Biophysica Acta*, 302: 420–428 (1973).
R. Jemmerson et al., "Monoclonal Antibodies Block the Trypsin Cleavage Site on Human Placental Alkaline Phosphatase", *FEBS LETTERS*, 173(2): 357–359 (Aug. 1984).
F. A. Green, "Phospholipid Requirement for Rh Antigenic Activity", *The Journal of Biological Chemistry*, 243(20): 5519–5524 (1968).
F. A. Green, "The Mode of Attenuation of Erythrocyte Membrane Rh$_0$(D) Antigen Activity by 5.5'–Dithiobis–(2–Nitrobenzoic Acid) and Protection Against Loss of Activity ...", *Molecular Immunology*, 20(7) 769–755 (1983).
F. Melchers et al., "Enhancing Stability Against Heat Denaturation of *E. coli* Wild Type and Mutant β–Galactosidase in the Presence of Specific ...", *Biochem. and Biophys. Res. Comm.*, 40(3): 570–575 (1970).
W. P. Levy et al., "Amino Acid Sequence of a Human Leukocyte Interferon", *Proc. Natl. Acad. Sci. USA*, 75(10): 6186–6190 (Oct. 1981).
"Albumin Complexes May Further Enzyme Therapy", *Chem. Eng. News*, 19–21 (Sep. 30, 1985).
Bird et al. "Single–Chain Antigen–Binding Proteins", *Science*, 242: 423–426 (1988).
Ben–Yoseph et al. "Antibody–Mediated Thermal Stabilization of Human Hexosaminidases", *Immunochemistry*, 12: 221–226 (1975).
Sandhu, *Crit. Rev. Biotech*, 12:437, 1992.
Wilhelm et al., *Crit. Rev. Eukaryotic Gene Express.*, 2:111, 1992.

*Primary Examiner*—Frank C. Eisenschenk
*Attorney, Agent, or Firm*—Foley & Lardner

[57] ABSTRACT

A recombinant chimeric polypeptide is produced that contains a biologically active entity and a binding entity, that displays biologically active and is inactivation resistant. The biologically active entity corresponds, for example, to an enzyme and the binding entity corresponds, for example, to an antibody. The entities interact to form a structure analagous to an antibody-antigen complex. Thus, the inactivation-resistant complex displays prolonged activity under conditions characterized by disrupting temperature, the presence of a proteolytic enzyme, disrupting pH, the presence of an oxidizing agent and/or the presence of an alcohol, among others.

11 Claims, 13 Drawing Sheets

FIG. 9

```
  1 GATATTGTCC TCACTCAATC GCCAGCAATC ATGTCTGCAT CTCCAGGGGA
 51 AAAGGTCACC ATGACCTGCA GGGCCAGCTC AAGTGTAAGT TCCAGTTACT
101 TGCACTGGTA CCAGCAGAAG CCCCCAAACT CTGGATTTAT
151 AGCACATCCA ACTTGGCTTC TGGAGTCCCT GCTCGCTTCA GTGGCAGTGG
201 GTCTGGGACC TCTTACTCTC TCACAATCAG CAGTGTGGAG GCTGAAGATG
251 CTGCCACTTA TTACTGCCAG CAGTACAGTG GTTACCCACT CACGTTCGGA
301 GGGGGGACCA AGCTGGAAAT AAAACGGGCT GATGCTGCAC CAACTGTATC
351 CATCTTCCCA
```

FIG. 10

```
  1  CAGGTCAAGC TGCAGGAGTC TGGGGGAGGC TTAGTGCAGC CTGGAGGGTC
 51  CCGGAAACTC TCCTGTGCAG CCTCTGGATT CACTTTCAGT AGCTTTGGAA
101  TGCACTGGGT TCGTCAGGCT CCAGAGAAGG GGCTGGAGTG GGTCGCATAC
151  ATTAGTAGTG GCAGTAGTAC CCTCCACTAT GCAGACACAG TGAAGGGCCG
201  ATTCACCATC TCCAGAGACA ATCCCAAGAA CACCCTGTTC CTGCAAATGA
251  AACTACCCTC ACTATGCTAT GGACTACTGG GGTCAAGGAA CCTCAGTCAC
301  CGTCTCCTCA GCCAAAACGA CACCCCCATC TGTCTATCCA CTGGCTCCTG
351  TGTGTGGAGA
```

FIG. 11

```
   1 GATATTGTCC TCACTCAATC GCCAGCAATC ATGTCTGCAT CTCCAGGGGA AAAGGTCACC
  61 ATGACCTGCA GGGCCAGCTC AAGTGTAAGT TCCAGTTACT TGCACTGGTA CCAGCAGAAG
 121 TCAGGTGCCT CCCCCAAACT CTGGATTTAT AGCACATCCA ACTTGGCTTC TGGAGTCCCT
 181 GCTCGCTTCA GTGGCAGTGG GTCTGGGACC TCTTACTCTC TCACAATCAG CAGTGTGGAG
 241 GCTGAAGATG CTGCCACTTA TTACTGCCAG CAGTACAGTG GTTACCCACT CACGTTCGGA
 301 GGGGGGACCA AGCTGGAAAT AAAACGGGCT GATGCTGCAC CAACTGTATC CATCTTCCCA
 361 GGTGGCGGTG GCTCGGGCGG TGGTGGGTCG GGTGGCGGCG GATCTCAGGT CAAGCTGCAG
 421 GAGTCTGGGG GAGGCTTAGT GCAGCCTGGA GGGTCCCGGA AACTCCTCTG TGCAGCCTCT
 481 GGATTCACTT TCAGTAGCTT TGGAATGCAC TGGGTTCGTC AGGCTCCAGA GAAGGGGCTG
 541 GAGTGGGTCG CATACATTAG TAGTGGCAGT AGTACCCTCC ACTATGCAGA CACAGTGAAG
 601 GGCCGATTCA CCATCTCCAG AGACAATCCC AAGAACACCC TGTTCCTGCA AATGAAACTA
 661 CCCTCACTAT GCTATGGACT ACTGGGGTCA AGGAACCTCA GTCACCGTCT CCTCAGCCAA
 721 AACGACACCC CCATCTGTCT ATCCACTGGC TCCTGTGTGT GGAGATCTAG AGGTGGCGGT
 781 GGCTCGGGCG GTGGTGGGTC GGGTGGCGGC GGATCTGGTG GCGGTGGCTC GGGCGGTGGT
 841 GGGTCGGGTG GCGGCGGATC TAGATCCTTA CCCAATATCA CCATTTTAGC AACCGGCGGG
 901 ACCATTGCCG GTGGTGGTGA CTCCGCAACC AAATCTAACT ACACAGTGGG TAAAGTTGGC
 961 GTAGAAAATC TGGTTAATGC GGTGCCGCAA CTAAAAGACA TTGCGAACGT TAAAGGCGAG
1021 CAGGTAGTGA ATATCGGCTC CCAGGACATG AACGATAATG TCTGGCTGAC ACTGGCGAAA
1081 AAAATTAACA CCGACTGCGA TAAGACCGAC GGCTTCGTCA TTACCCACGG TACCGACACG
1141 ATGGAAGAAA CTGCTTACTT CCTCGACCTG ACGGTGAAAT GCGACAAACC GGTGGTGATG
1201 GTCGGCGCAA TGCGTCCGTC CACGTCTATG AGCGCAGACG GTCCATTCAA CCTGTATAAC
1261 GCGGTAGTGA CCGCAGCTGA TAAAGCCTCC GCCAACCGTG GCGTGCTGGT AGTGATGAAT
1321 GACACCGTGC TTGATGGCCG TGACGTCACC AAAACCAACA CCACCGACGT AGCGACCTTC
1381 AAGTCTGTTA ACTACGGTCC TCTGGGTTAC ATTCACAACG GTAAGATTGA CTACCAGCGT
1441 ACCCCGGCAC GTAAGCATAC CAGCGACACG CCATTCGATG TCTCTAAGCT GAATGAACTG
1501 CCGAAAGTCG GCATTGTTTA TAACTACGCT AACGCATCCG ATCTTCCGGC TAAAGCACTG
1561 GTAGATGCGG GCTATGATGG CATCGTTAGC GCTGGTGTGG GTAACGGCAA CCTGTATAAA
1621 TCTGTGTTCG ACACGCTGGC GACCGCCGCG AAAACCGGTA CTGCAGTCGT GCGTTCTTCC
1681 CGCGTACCGA CGGGCGCTAC CACTCAGGAT GCCGAAGTGG ATGATGCGAA ATACGGCTTC
1741 GTCGCCTCTG GCACGCTGAA CCCGCAAAAA GCGCGCGTTC TGCTGCAACT GGCTCTGACG
1801 CAAACCAAAG ATCCGCAGCA GATCCAGCAG ATCTTCAATC AGTACTAA
```

USE OF ANTIBODY/ANTIGEN INTERACTIONS TO PROTECT BIOLOGICALLY ACTIVE PROTEINS AND PEPTIDES

This application is a continuation of application Ser. No. 08/081,410, filed Jun. 22, 1993 now abandoned which is a continuation in part of U.S. Ser. No. 07/938,505, filed Aug. 31, 1992, now abandoned, which is a continuation of U.S. Ser. No. 07/205,748, filed Jun. 21, 1988, now abandoned.

BACKGROUND OF THE INVENTION

This invention relates to the use of antibody/antigen interactions to protect biologically active entities against in vivo and in vitro inactivation.

Biologically active entities, such as enzymes, hormones, growth factors, antibodies and drugs, are used in a variety of medical and industrial applications in which their useful life may be shortened by inactivation. Such inactivation may result from physical, chemical or biological processes or conditions, or by self-destruction in the case of certain enzymes, occurring concurrently with the processes of the desired activity in a particular application; the inactivation may result from a combination of such inactivating processes. In some cases the inactivation occurs rapidly, necessitating frequent replacement of the active entity.

V. V. Mozhaev et al, *Enzyme Microb. Technol.*, 1984, Vol. 6, page 50 et seq., review structure-stability relationships in proteins and existing approaches to stabilizing proteins. In *Chemical & Eng'r News*, Sep. 30, 1985, page 19 et seq., there is a description of albumin/enzyme complexes that are resistant to proteolytic and heat inactivation, while U.S. Pat. No. 4,179,337 refers to polyethylene glycol/enzyme complexes which are also inactivation-resistant.

Biologically active entities are employed in a labelled form in different environments, for example, in immunological detection and diagnostic processes. The label may typically be a radioactive isotope label, enzyme label, fluorescent label or a label which can be determined photometrically. One limitation on the selection of the label is that it should not react with, and potentially inactivate, a site of desired biological activity of the biologically active entity.

Several solutions have been proposed to slow deterioration of activity in specific cases where a biologically active entity is subjected to inactivating conditions. However, no general approach has previously been formulated to counter the different inactivation processes with one type of agent.

SUMMARY OF THE INVENTION

It is therefore an object of this invention to employ interactions between antibodies and biologically active antigens to effect a modulation, and particularly a prolongation, of their activity.

It is a further object of this invention to provide a biologically active entity stabilized against inactivation of a desired biological activity.

It is yet another object of the present invention to provide a mechanism for slow-release of a biologically active entity in order to provide sustained activity.

In accomplishing the foregoing objects, there has been provided, in accordance with one aspect of the present invention, a method of producing a biologically active complex characterized by an enhanced resistance to inactivation, comprising the steps of (A) providing a complex comprised of a molecule which is biologically active and an antibody entity that recognizes that molecule, said complex being biologically active; and (B) measuring a prolongation of biological activity, when the complex is subjected to a condition that inactivates the uncomplexed molecule, relative to inactivation of the molecule by the condition in question. In preferred embodiments, step (A) comprises exposing the biologically active molecule to either polyclonal antibody or a monoclonal antibody that recognizes the molecule. In another preferred embodiment, the antibody entity is an antibody fragment or an antigen-binding protein.

In accordance with another aspect of the present invention, a complex has been provided that comprises (i) a molecule having a biological activity and (ii) an antibody entity recognizing that molecule, which complex displays a biological activity that is inactivation-resistant, relative to that of the free molecule. In a preferred embodiment, the molecule is an enzyme.

SUMMARY OF INVENTION

In accordance with another aspect of the present invention, a chimetic protein is provided comprising (i) a single-chain antibody specific for a biologically active entity and (ii) the biologically active entity itself, fused together as a single polypeptide chain that is stabilized against inactivation of the biologic activity.

In one embodiment of the foregoing aspect, there is provided a recombinant, chimeric polypeptide of a biologically active entity and an antibody entity in a single polypeptide chain comprised of three distinct regions, wherein (i) a region (A) of said recombinant complex includes a first domain which is capable of biological activity, and a second domain which contains an epitope for binding to another portion of said recombinant complex;

(ii) a region (B) of said recombinant complex includes an antibody-like domain comprising polypeptide portions of the light and heavy chains of the hypervariable region of an antibody that binds to said epitope of region (A), said light and heavy chains being linked by a first linker portion of said polypeptide;

(iii) and a region (C) of said recombinant complex includes a second polypeptide linker portion linking region (A) and region (B);

and wherein said linear polypeptide assumes a conformation such that said antibody-like domain of said region (B) is bound in an antibody-antigen-like fashion to said epitope of region (A) and said region (A) is able to effect said biological activity;

and wherein said antibody-antigen-like binding confers upon said recombinant complex resistance to a deactivating condition with respect to said biological activity.

A method has also been provided, in accordance with still another aspect of the present invention, that comprises the steps of (1) providing a complex comprised of a molecule which is biologically active and an antibody entity that recognizes the molecule, said complex presenting at least one binding site for a labelling agent; (2) exposing the complex to the labelling agent such that the labelling agent is bound to the binding site; and then (3) effecting a disassociation of the complex to release the molecule carrying said labelling agent. In a preferred embodiment, the biologically active molecule is itself an antibody.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention is illustrated in the accompanying drawings, in which:

FIG. 9 is the nucleotide sequence of IgG light chain variable region. A cDNA clone coding for the variable region (SEQ ID NO:13) of the IgG light chain was isolated from cells expressing monoclonal antibody #12, recognizing asparaginase II and protecting it from trypsin digestion. The gene was isolated and sequenced as described in the text.

FIG. 10 is the nucleotide sequence of IgG heavy chain variable region (SEQ ID NO:14). A cDNA clone coding for the variable region of the IgG heavy chain was isolated from cells expressing monoclonal antibody #12, recognizing asparaginase II and protecting it against trypsin digestion. The gene was isolated and sequenced as described in the text.

FIG. 11 is the nucleotide sequence of the chimeric gene (SEQ ID NO:15). The chimeric gene consists of the following: light chain variable region (1–360); first linker sequence (361–405—underlined); heavy chain variable region (406–765); second linker region (766–867—underlined); ansB gene sequence (868–1848).

DETAILED DESCRIPTION OF THE PREFERRED EMBODIMENTS

Figure 1:
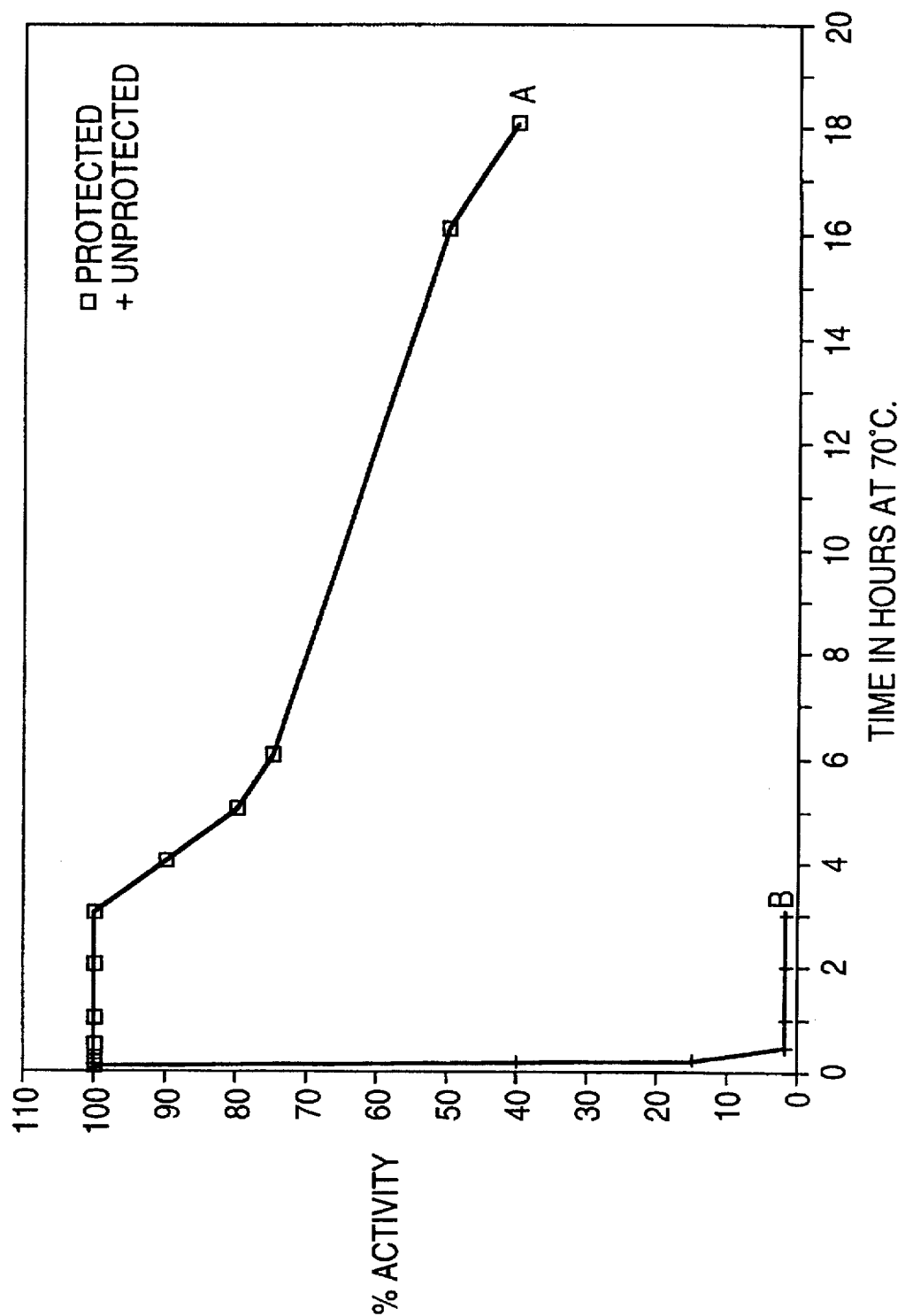
FIG. 1 is a graph depicting the loss in activity over time at 70° C. of α-amylase compared with the same enzyme stabilized in accordance with the present invention.

It has been discovered that a wide variety of biologically active molecules can be rendered inactivation-resistant by exploiting antibody/antigen interactions to protect vulnerable sites on such molecules from the harmful effects of any inactivation process, thereby dramatically slowing loss of biological activity. Since the interaction of an antibody with its antigen has been viewed heretofore as the first step in the ultimate destruction of the antigen, the use of an antibody/ antigen interaction, pursuant to the present invention, to prolong the biological activity of an antigen represents an original approach which would not have been considered heretofore. More generally, the innovative use of an antibody/antigen interaction for protective purposes, rather than for destroying biologically active entities, as defined below, is a departure from the conventionally recognized use of antibody/antigen interactions.

To achieve a prolongation of biological activity in accordance with the present invention, a binding entity (as further defined below) is prepared that recognizes at least one site on a molecule ("biologically active entity"), that site being necessary to activity and normally subject to inactivation under certain conditions, such as disrupting temperature or pH or the presence of some agent like a proteolytic enzyme, an alcohol or an oxidant. A suitable binding entity in this context can be an antibody which is raised by challenging the immune system of a standard laboratory animal with all or a portion of the biologically active entity. Alternatively, the binding entity can be an antigen-binding protein, as described below, which recognizes the biologically active entity. In any event, it is a routine matter to screen putative binding entities, pursuant to the present invention, to identify those having the requisite specificity, i.e., those that bind the biologically active entity in an inactivation-inhibitive manner without unduly lessening biological activity.

(i) "Biologically Active Entity"

More specifically a biologically active entity suitable for the present invention can be any molecule that promotes or actively participates in a desired biological reaction and that has at least one first site responsible for, contributing to or participating in the desired biological reaction. Generally, a suitable biologically active entity will additionally have at least one second site which is essentially noncontributing to the desired biological reaction.

By "essentially noncontributing," it is intended that the at least one second site is not essential to the performance of the first site in the desired biological reaction. In particular, the second site may play a role in processes that result in inactivation of the biologically active entity, with respect to the desired biological activity. This inactivation may result from a physical, chemical or biological process or from a combination of such processes.

Biologically active entities which are used in the present invention can be enzymes, hormones, growth factors and antibodies, for example, as well as chemical species which effect biological change, such as drugs and medicines. Suitable biologically active entities include such enzymes as amylases, like α-amylase and β-amylase; glucoamylase, glucose isomerase, invertase; proteases like trypsin and subtilisin; pectinase, L-asparaginase, α-1,4-glucosidase, cholesteryl esterase, uricase, catalase, superoxide dismutase and glucose-6-phosphatase. Other biologically active entities are interferon, tissue plasminogen activator and muteins thereof, and such antibodies as CEA (carcinogen embryonic antigen), antibodies to HTLV, and antibodies to mouse IgG.

For enzymes, hormones and the like, there will typically be a plurality of the active first sites and, generally, a plurality of the second sites. Depending on the particular application, either the first or second sites, but not both, will participate in the antibody/antigen interaction. When the binding entity (see below) is an antibody entity, such sites will be epitopes to which the antibody entity will bind. In the case of drugs and medicines, the first site may be a chemical configuration or ligand responsible for the desired biological activity, and the second site may likewise be a chemical configuration or ligand.

Preferably, the first and second sites are spaced apart so that there is no stearic or other interference of the first site by the second site, after binding with the binding entity.

(ii) "Binding Entity"

The binding entity is, in particular, an antibody entity that "recognizes" (binds to) a specific portion or site of the biologically active entity. An antibody entity suitable for the present invention can be polyclonal antibody, one or more monoclonal antibodies, or an amino-acid sequence which contains the variable regions of an antibody. An antibody entity can also comprise hypervariable regions derived, respectively, from the heavy and light chains of an antibody, which regions could be linked:

in their natural (in vivo) configuration, e.g., as in a Fab fragment, via chemical modification, using bifunctional linkers, to effect a crosslinking in vitro, or through a linking entity comprised of a variable-length peptide chain, thereby to provide a single-chain antibody or so-called "antigen binding protein," as disclosed, for example, in U.S. Pat. No. 4,704,692, the contents of which are hereby incorporated by reference.

In another embodiment, DNA's encoding the biologically active entity and the antibody entity may be covalently joined in a "head-to-tail" fashion, generating a single "chimeric" gene. Expression of this chimeric gene results in a single polypeptide containing both active and an antibody regions. These regions preferably are connected by a linking peptide, the length of which varies according to the distance between the linker and the active and binding sites. The linker provides flexibility and spacing, thereby facilitating the interaction of the two sites.

In order to facilitate maximal activity, binding and protection of the complex, it may be necessary to refold the complexes. A variety of standard protein refolding protocols may be used along with modifications thereto, depending upon the nature of the particular complex to be synthesized. For example, see Fiona et al., *Biochem. J.* 240:1–12 (1986).

An antibody entity within the present invention thus should be capable of binding to the second site(s) of the biologically active entity so as to prevent substantially or delay participation by the second site(s) in a process that leads to a deterioration of the desired biological activity to which at least one first site relates. The antibody entity may be formed in an immunological response, wherein the second site acts as an antigenic or antibody recognition site; this is not essential, however, as the antibody entity need only bind the second site so that it does not participate in an inactivation process. In addition, the antibody entity should not bind or interfere with the sites responsible for the desired biological activity to such a degree that the desired biological activity cannot serve a useful purpose.

Procedures are well-known for producing polyclonal antibodies and monoclonal antibodies, as well as fragments of antibodies, that will bind to a biologically active molecule. A suitable procedure can involve immunizing a rabbit or other standard laboratory animal with the biologically active entity, which may have been modified beforehand so as to "mask" the desired first sites and prevent the generation of inhibitory antibodies which recognize the first sites. For example, an antibody could be produced initially that binds a first site; then the complex of that antibody and the biologically active molecule would be used as the antigen to raise noninhibitory polyclonal sera. By means of conventional techniques, antisera taken from the animal can then be used as a source for antibody that binds the biologically active entity without destroying its activity, i.e., to produce antibody recognizing the second site(s), but not the active site, of the biologically active entity.

If this technique is employed without protection of the desired first site, e.g., if such sites have not been identified, routine testing of different polyclonal antibody samples thereby developed can be carried out to identify those which will recognize the biologically active entity and form an active complex that is inactivation-resistant.

By the same token, conventional somatic-fusion procedures, as outlined, for example, by Kennett et al, *Curr. Top. Microbiol. Immunol.* 81: 77–91 (1978), can be employed to produce monoclonal antibodies suitable for use in the present invention. For example, mice can be immunized in a known manner with the biologically active entity, or a part of it. Spleen cells of the immunized mice are then removed and fused with an immortalizing cell line, such as murine myeloma line BALB/C NS-lAg4-1 (ATCC No. TIB18), according to the method of Kohler and Milstein, see, e.g., *Nature* 256: 495–97 (1975), and the resulting fusion products are screened for those that survive in culture and produce monoclonal antibody of the desired specificity. In this way, different hybridomas can be tested for production of monoclonal antibody that form, with the biologically active entity, a complex which displays prolonged activity (relative to the free molecule) under inactivating conditions.

In accordance with the present invention, a biologically active entity can be analyzed to identify specific sites which are to be bound by the binding entity. For example, fragments of the biologically active entity that do not include any active sites can be used as antigen to produce antibody which binds the biologically active entity without interfering with its activity.

When the biologically active entity is itself an antibody, its antigen binding site can be protected, pursuant to the present invention, using either antigen normally bound by the antibody or an anti-idiotypic antibody, i.e., an antibody that recognizes the antigen binding site.

(iii) "Inactivation"

The biologically active entities employed in this invention may be inactivated as a result of physical, chemical or biological processes which may occur in the working environment of the entity. For example, disruptive increases or decreases in temperature, as well as oxidation may, result in inactivation. In the case in which the biologically active entity is an enzyme, inactivation may also result from enzymatic self-destruction.

A biologically active entity within the present invention can be employed in any environment in when the entity has previously been employed, as well as in environments where it has not been heretofore practical to use it because of short-lived activity. For example, use of enzymes as drugs or therapeutic agents is limited by their biodegradation or inactivation in the body; the present invention provides a means for overcoming this problem.

By the same token, an antibody which is used, according to the present invention, as a biologically active entity can be labelled or complexed with a desired drug, agent or other species without interfering with an active site of the antibody which is needed in the immunogenic or diagnostic process. Thus, antibodies are often chemically modified for the purpose of labelling. Most of these reactions are random and leave a certain percentage of the antibody inactive, due to the chemical modification of binding sites. This can be prevented, pursuant to the present invention, if before the chemical modification (labelling) the antibody is reacted with its antigen (preferably, with antigen immobilized on a solid surface) so that the binding site is occupied and protected. Thereafter, when the labelling procedure is completed, the antibody/antigen complex can be dissociated, for example, with low pH buffer, and the labelled antibody collected and used.

Conversely, if an antigen is to be labelled, its antibody can immobilized, the antigen added, and labelling (and subsequent slution) carried out to remove the antibody.

Growth factors like interferon and erythropoietin have a very short half-life in serum, mainly due to enzymatic degradation. This problem is compounded when the drug is produced by engineered organisms within normal glycosylation is not effected and, as a consequence, carbohydrate residues found in the naturally-occurring molecule are missing. In the case of erythropoietin, these residues provide protection against enzymatic degradation. Specific antibodies can provide similar protection, allowing for the use of the less expensive, genetically-engineered erythropoietin. Growth factors like epidermal growth factor (EGF), which are used to affect growth and proliferation of certain cell types, have an effectiveness that is diminished by degrading enzymes secreted by growing cells. Their efficacy can therefore be improved, in accordance with the present invention, by binding with an antibody entity.

Animal growth hormone can be used to increase body weight or milk production in farm animals. It is believed, however, that rapid inactivation of the injected hormone by proteolytic and other enzymes in vitro has made it necessary to use daily injections of the hormone, which is cumbersome. But protection of the growth hormone by binding the hormone with specific antibodies, in accordance with the invention, can protect the hormone from enzyme degradation without unduly reducing its potency. As a result, the effective hormone level can be maintained with lower doses and fewer injections.

In addition to protecting enzymes against inactivation by other enzymes, the present invention can be used protect an enzyme against self-degradation. For example, proteolytic enzyme, such as the subtilisin used in many detergents, can be protected against self-degradation by specific antibody entities pursuant to the present invention.

In accordance with the present invention, it is also possible to use a labelling entity which might otherwise be unsuitable as a result of side reactions affecting the desired site of activity. Thus, the desired site is initially bound to the binding entity to form a complex, thereafter the complex is labelled with the labelling agent by conventional procedures, the labelling entity being bound by the at least one second site. After the labelling entity is bound to the a second site, the binding entity is removed, by conventional procedures, from the labelled complex to provide the labelled biologically active entity in which the first site is free, the labelling agent being bound so that it is no longer available for reaction with the first site.

By means of the present invention, a biologically active species can be complexed with the binding entity so as to assure the slow release over time of the species. In this way a single high dosage of the (complexed) species, which might otherwise be unacceptable because of toxicity or side effects, may be employed and frequent administrations (or higher dosages of a rapidly degraded species) consequently avoided.

The present invention is further described below by reference to the following, illustrative examples.

EXAMPLE 1

The Effect of Temperature on Antibody Protected and Unprotected α-Amylase

As described in greater detail below, comparison tests were carried out on α-amylase and α-amylase stabilized in accordance with the invention. In FIG. 1, Plot A shows that the stabilized α-amylase in accordance with the invention still had 100% activity after three hours, and 50% activity after 16 hours, at 70° C., while α-amylase not stabilized in accordance with the invention (Plot B) was completely inactivated (0% activity) after only 15 minutes at the same temperature. A similar, relative resistance to heat-inactivation is evident from a comparison of Plot C (stabilized α-amylase) with Plot D (free enzyme) in FIG. 2.

A human salivary α-amylase (EC 3.2.1.1; Sigma catalog No. A052) stock solution (100 units/ml, or 0.1 mg protein/ml) was made up in 5 mM $CaCl_2$ and 0.9% NaCl. To obtain a "protected" form of the enzyme, the volume equivalent of 35 units of α-amylase solution was added 245 ml of a 5 mM $CaCl_2$/0.9% NaCl solution containing rabbit polyclonal (IgG) anti-human salivary α-amylase antibody purchased from Sigma Chemical Company (catalog No. A8273; protein content: 2.85 mg/ml; estimated specific antibody content: 0.1425 mg/ml). The mixture was then incubated overnight at 4° C.

The molar ratio of α-amylase to specific IgG of the resulting test composition was nominally 2:1, and an enzyme activity of 58.8 units/ml was measured using a commercial kit (No. 575-UV; product of Sigma Chemical Co., St. Louis, Mo.) which monitors enzyme-mediated maltose production as a function of increased absorbance at 340 nm . A control (unprotected) composition with the same activity was produced, pursuant to the same basic protocol, by mixing α-amylase with normal mouse IgG, i.e., IgG from a mouse that was not exposed to human α-amylase.

Sample dilutions (100 ml; 2.94 units/ml) with $CaCl_2$/NaCl solution of the test and comparison compositions, respectively, were placed in a Gilford "Response" UV-VIS spectrophotometer which had been previously temperature-adjusted to a particular temperature. After a 5-minute incubation, each sample was removed and cooled in ice water. After the spectrophotometer had been readjusted to 30° C., the samples were reintroduced, respectively, equilibrated to 30° C., and tested (using the above-mentioned Sigma kit) for enzyme activity, as measured via an increase in absorbance at 340 nm.

Both the protected and unprotected samples were subjected to the following temperatures: room temperature (RT; about 22°), 65°, 68°, 70°, 72°, 75°, 80°, 85° and 90° C. The linear rate constant at each temperature was determined and percentage activity calculated as:

$$\frac{\text{Rate at } T°}{\text{Rate at } RT} \times 100.$$

Figure 2:
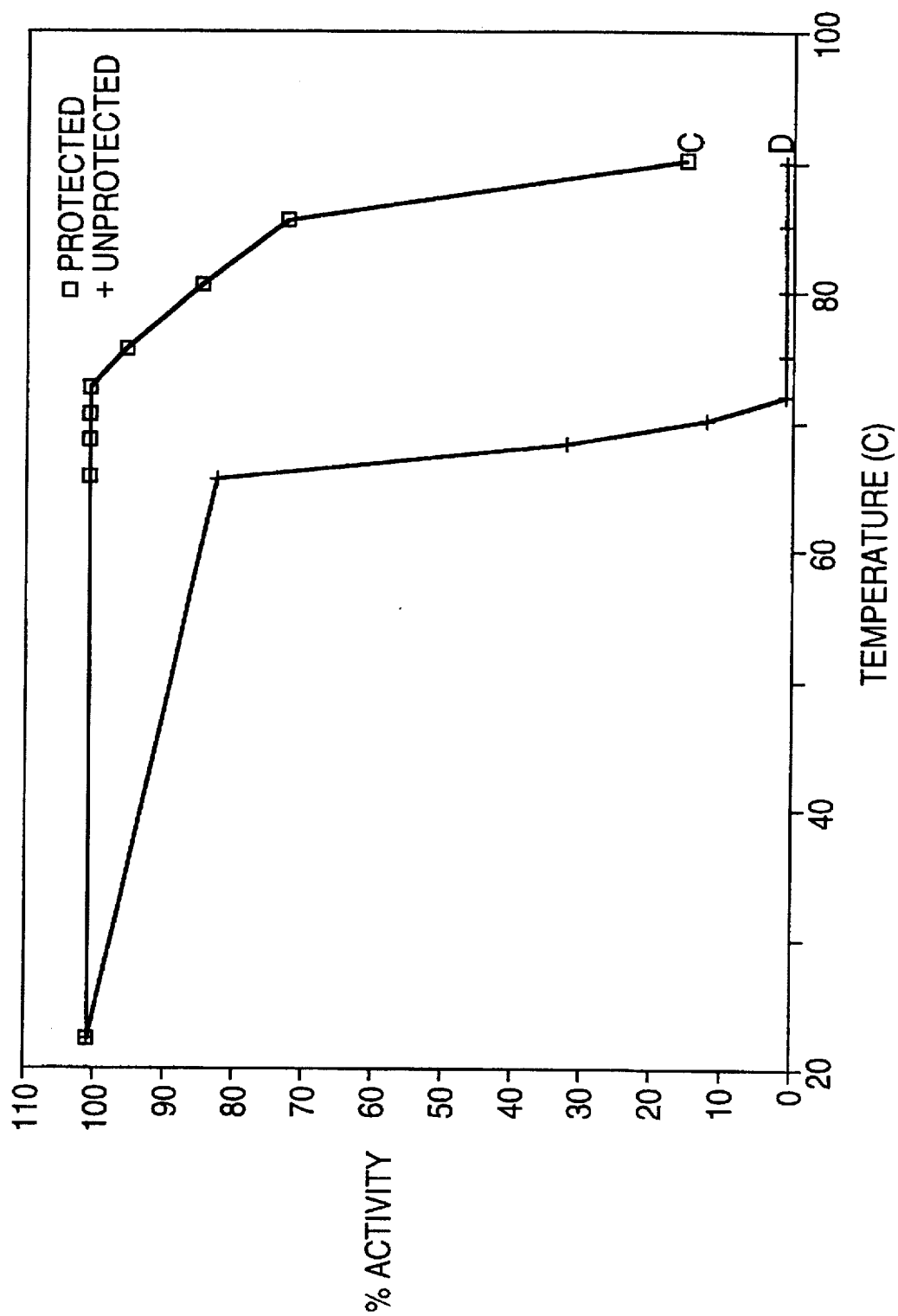
FIG. 2 is a graph showing the loss, with increasing temperature, in activity of the biologically active entity in FIG. 1, compared with the same entity stabilized in accordance with the present invention.

The plot thus obtained of percent activity versus temperature is shown in FIG. 2.

In a separate experiment, test and control dilutions were prepared as described above, and a 100 ml sample of unprotected or protected enzyme was added to each of five cuvettes of the Gilford spectrophotometer, and the temperature was adjusted to 70° C. At the end of 0, 5, 10, 15 and 30 minutes, respectively, one cuvette was taken out and cooled immediately in ice water. After the final incubation, the spectrophotometer was readjusted to 30° C., the cuvettes were reinserted and, after 5 minutes to allow for equilibration of the samples, each sample was tested for enzyme activity, as previously described.

For long-term incubations, a water bath set at 70° C. was used. Two tubes containing 1.5 ml aliquots of the protected and unprotected α-amylase dilutions, respectively, were incubated in the water bath for 1, 2, 3, 4, 5, 6, 16, 18 and 20 hours. At the end of each time, 100 ml of each sample were pipetted out into a cuvette and cooled in ice water. After five minutes, the two samples were then placed in the spectrophotometer, which had been adjusted to 30° C., and after five more minutes the enzyme activity of each sample was measured.

The linear rate constant for each incubation time was determined and % activity for a given incubation time calculated as follows:

$$\frac{\text{Rate at } 70° \text{ C. for time } T}{\text{Rate at } RT \text{ (0 incubation time at } 70° \text{ C.)}} \times 100$$

The plot of percentage activity versus incubation time at 70° C. is shown in FIG. 1.

Tests substantially similar to those described above were carried out with the enzymes subtilisin and glucoamylase. For both biologically active molecules, the use of polyclonal antibody pursuant to the present invention resulted in a prolongation of activity, under conditions of disruptively high temperature, relative to the unprotected enzyme. Thus, free subtilisin lost 50% of original activity in less than five minutes at 65° C., while the subtilisin-antibody complex retained over 50% of its activity for at least three hours at the same temperature. By the same token, unprotected glucoamylase lost 95% of its activity at 66° C. in only five minutes (half-life: about two minutes), whereas the protected enzyme was still over 50% active after three hours (half-life: >three hours).

EXAMPLE 2

The Effect of Trypsin on Antibody-Protected and Unprotected Asparaginase

A. Use of Polyclonal Antibody:

Mouse polyclonal anti-asparaginase sera was purified on a protein-A column and dialyzed for 17 hours against water.

The dialyzed IgG fraction was then concentrated by vacuum dialysis to a protein concentration of 100 mg per ml, the resulting concentrate ("antibody solution") having an assumed specific-IgG content of 5% Thereafter, 1.2 units of L-asparaginase (EC 3.5.1.1) dissolved in a 0.1M borate-HCL/0.1 mM EDTA buffer (pH 9.0) were mixed with 1.12 ml of antibody solution, giving a 1:1 molar ratio of enzyme to specific antibody, and the mixture was incubated overnight at 4° C. Water (0.82 ml at pH 9.2) was then added to give a final concentration of 0.6 units of protected asparaginase/ml.

The antibody-protected and unprotected samples of asparaginase (0.15 units per ml of each) were preincubated with 5 units per ml of trypsin (Sigma catalog No. T1005) in water pH 9.2 for 5 minutes at 37° C. The trypsin-treated samples were then transferred to two cuvettes in the thermal holder of a Gilford spectrophotometer previously set at 37° C. An equal volume of substrate (2 mM L-asparagine in water; pH 9.2) was then added and the conversion of L-asparagine (1 mM final) to L-aspartic acid was monitored at 197 nm at 37° C.

The results, as shown in Table 1 below, demonstrate the extremely low conversion rate of L-asparagine by the unprotected asparaginase in the presence of trypsin, as compared with asparaginase protected in accordance with the present invention.

TABLE 1

| Experiment | | Time for 50% Conversion of 1 mM L-Asparagine to L-Aspartic acid | % Conversion per minute |
|---|---|---|---|
| 1 | *AB Protected | 20.5 mins. | 2.5% |
|   | *Unprotected | **7.15 hrs. | 0.116% |
| 2 | *AB Protected | 20.5 mins. | 2.5% |
|   | *Unprotected | ***11.5 hrs. | 0.07% |

*Both protected and unprotected asparaginase were treated with 5 units/ml of trypsin at an asparaginase concentration of 0.15 units/ml.
**Obtained by extrapolation based on conversion per minute.
***Obtained by interpolation based on endpoint determination of conversion after 20 hours of incubation with the substrate.

B. Use of Various Monoclonal Antibodies:

Monoclonal antibodies (MAbs) to L-asparaginase were prepared according to the method of Kohler and Milstein. Fifty micrograms of L-asparaginase suspended in phosphate buffer and Complete Freund's Adjuvant (1:1 volume ratio) were injected intraperitoneally into each of four BALB-C mice. A day 12 post-injection, a first boost was given i.p. in the form of 50 micrograms of the enzyme in phosphate buffer. On day 15, the mice were bled and their antibody titer was determined by the ELISA method. Those with the highest titer were given a second boost of the same constituency and, three days later, were sacrificed and their spleen cells were removed for use in a somatic fusion.

After 7 days, the supernatants from growing hybridomas were tested by the ELISA method for positive reaction against L-asparaginase. The most promising hybrids were cloned by the "limiting dilution method," as disclosed by Lefkovits and Waldmann, LIMITING DILUTION ANALYSIS OF CELLS IN THE IMMUNE SYSTEM (Cambridge Univ. Press 1979). Six clones of producing monoclonal antibodies were obtained and were labelled No. 12, No. 19, No. 29, No. 33, No. 34 and No. 35, respectively.

Five samples of enzyme-antibody complex were prepared as follows. To samples containing 25 ml (0.05 units) of L-asparaginase were added antibody in an amount to provide ratios of 1, 2, 6, 10 and 20 mg protein per unit of enzyme, respectively. Water was added to give a final sample volume of 500 ml. Samples were prepared in this way with monoclonals No. 12, No. 29, No. 34 and No. 35, and with a bovine serum albumin (BSA), and were stored at 4° C. overnight before testing, as described below.

In addition, 1.5 equivalents (3.75 mg) of each enzyme-specific MAb were added to 0.5 unit (2.33 mg) of L-asparaginase. In like fashion, samples of enzyme-antibody complex were prepared using four MAbs (Nos. 12, 29, 34 and 35) and three MAbs (Nos. 12, 29 and 34), respectively, in combination.

A Gilford "Response" spectrophotometer with temperature-controlled, 6-position, 10 mm-cuvette holder was set at 37° C., and 50 ml of each of the five samples prepared using one monoclonal antibody was added to separate cuvettes. Water (35 ml) and trypsin (15 ml; 1.5 units) were added and the solutions incubated at 37° C. for five minutes. At the end of this time the cuvettes were taken out and cooled in ice water. After spectrometer was readjusted to 25° C., the cuvettes were reinserted and allowed five minutes to equilibrate. Water (100 ml; pH 9.0) and substrate (200 ml) were added and mixed with a pasteur pipette. The conversion rate (decrease in absorbance/minute at 197 nm) of L-asparagine to L-aspartic acid was determined for each sample.

In a separate experiment, 65 ml (0.065 units) of each of the four multi-MAb samples were added to separate cuvettes of the spectrophotometer. Water (15 ml), trypsin (20 ml, 2 units) and substrate (200 ml) were added, and the conversion rate of L-asparagine to L-aspartic acid was determined for each sample. A control sample, prepared by diluting 25 ml of enzyme with water to a final volume of 650 ml, was also run with and without the addition of trypsin.

Figure 3:
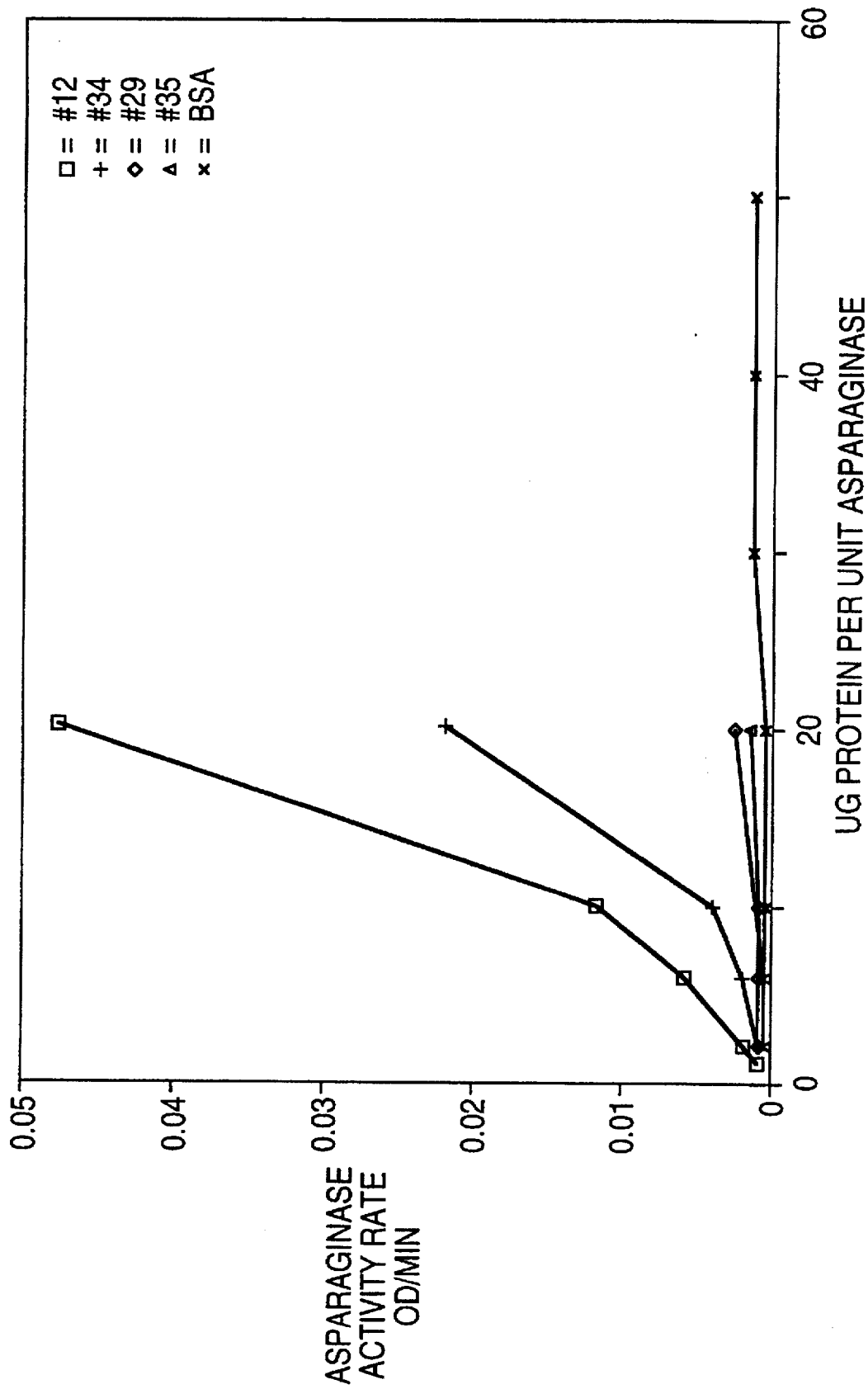
FIG. 3 is a graph wherein the residual activity (in the presence of trypsin) of the biologically active entity, asparaginase, is plotted as a function of the increase in concentration of different antibody entities, or other proteins, employed to protect biological activity in accordance with the present invention.
Figure 4:
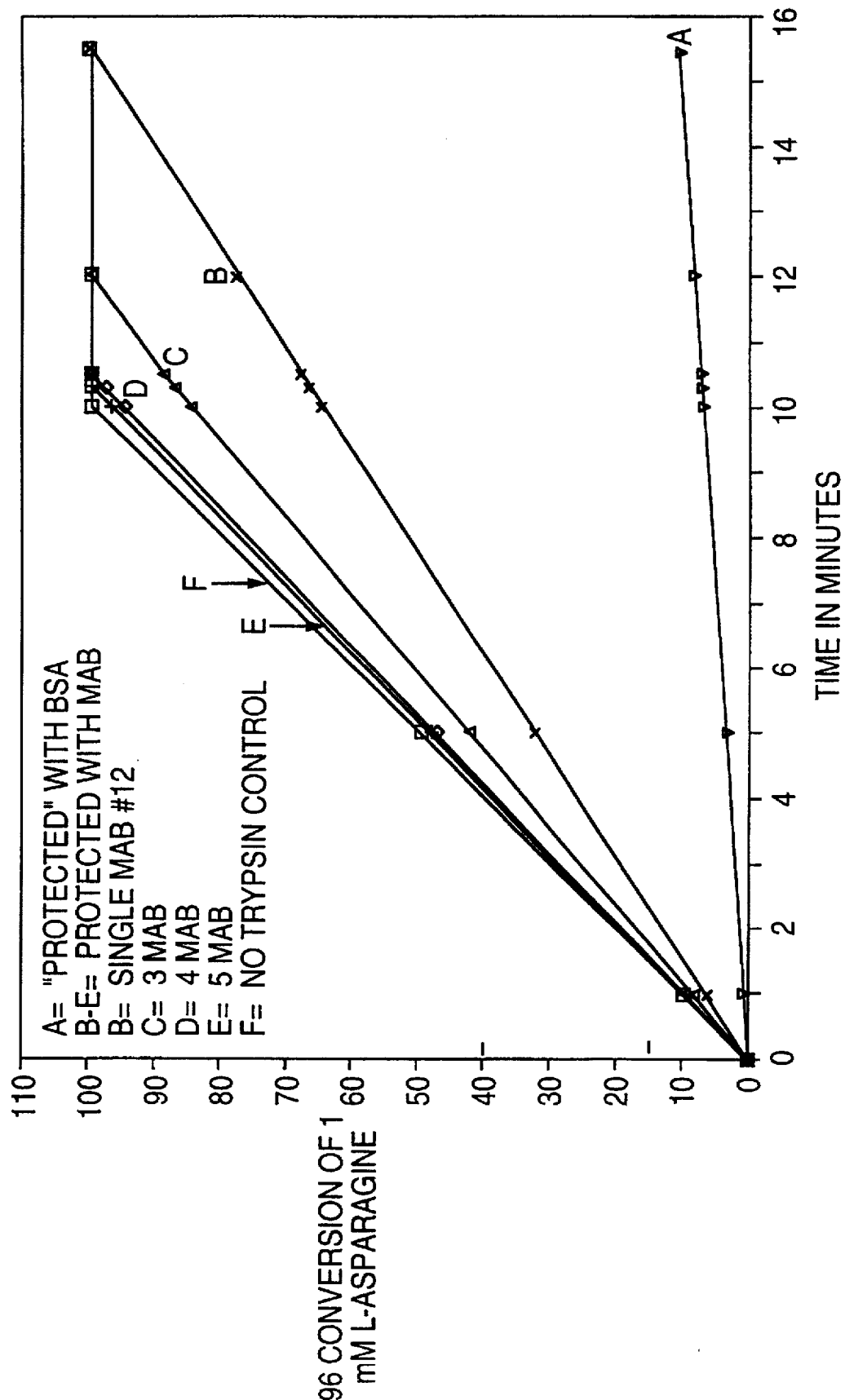
FIG. 4 is a graph showing the residual activity of asparaginase in the presence of trypsin, when the enzyme is protected with different combinations of monoclonal antibody in accordance with the present invention with time.

A plot of L-asparaginase residual activity versus antibody concentration (mg protein added per unit of L-asparaginase) for each of four single-MAb samples and for BSA-MAb sample is shown in FIG. 3. The percent conversion of 1 mM of L-asparagine to L-aspartic acid versus time is plotted in FIG. 4 for the multi-MAb samples. These results demonstrate that (1) the degree of protection varied from MAb to MAb, with No. 12 the most effective, and (2) an unrelated protein (BSA) provided virtually no protection. A significant level of protection was achieved with MAb No. 12 alone—unprotected, trypsin-challenged enzyme lost over 90% of its activity under the same conditions—but protection approximating that of the unchallenged control required the use of four or five monoclonal antibodies.

EXAMPLE 3

Protection of L-Asparaginase Against the Effect of Disrupting pH

Three equivalents (10.26 mg) of each of four MAbs from Example 2 (Nos. 12, 29, 34 and 35) were added to 45 ml of L-asparaginase (0.9 units, 3.214 mg) to give a final volume was 2.1 ml. The sample was incubated overnight at 4° C. A control sample was prepared by diluting 100 ml of L-asparaginase to 2 ml with water.

Both samples from were kept in ice and were adjusted to pH 3 with dilute HCl. A 50-ml aliquot of each was added to a cuvette, 150 ml of water (pH 9.2) with 200 ml of substrate were added, and the solutions were mixed. The activity of each sample, in terms of conversion rate of L-asparagine to L-aspartic acid, was determined (at zero time, $T_0$) in a Gilford "Response" spectrophotometer which had been set to 25° C.

The two samples were then placed in a water bath set at 37° C. Aliquots (50 ml) of each were taken at intervals of 5, 15, 45 and 65 minutes, and after 3 and 18 hours. The activity of each of these samples was determined as above. The percentage activity for a given incubation time ($T_x$) was calculated as follows:

$$\frac{\text{Rate of conversion at } T_x}{\text{Rate of conversion at } T_0} \times 100.$$

Figure 5:
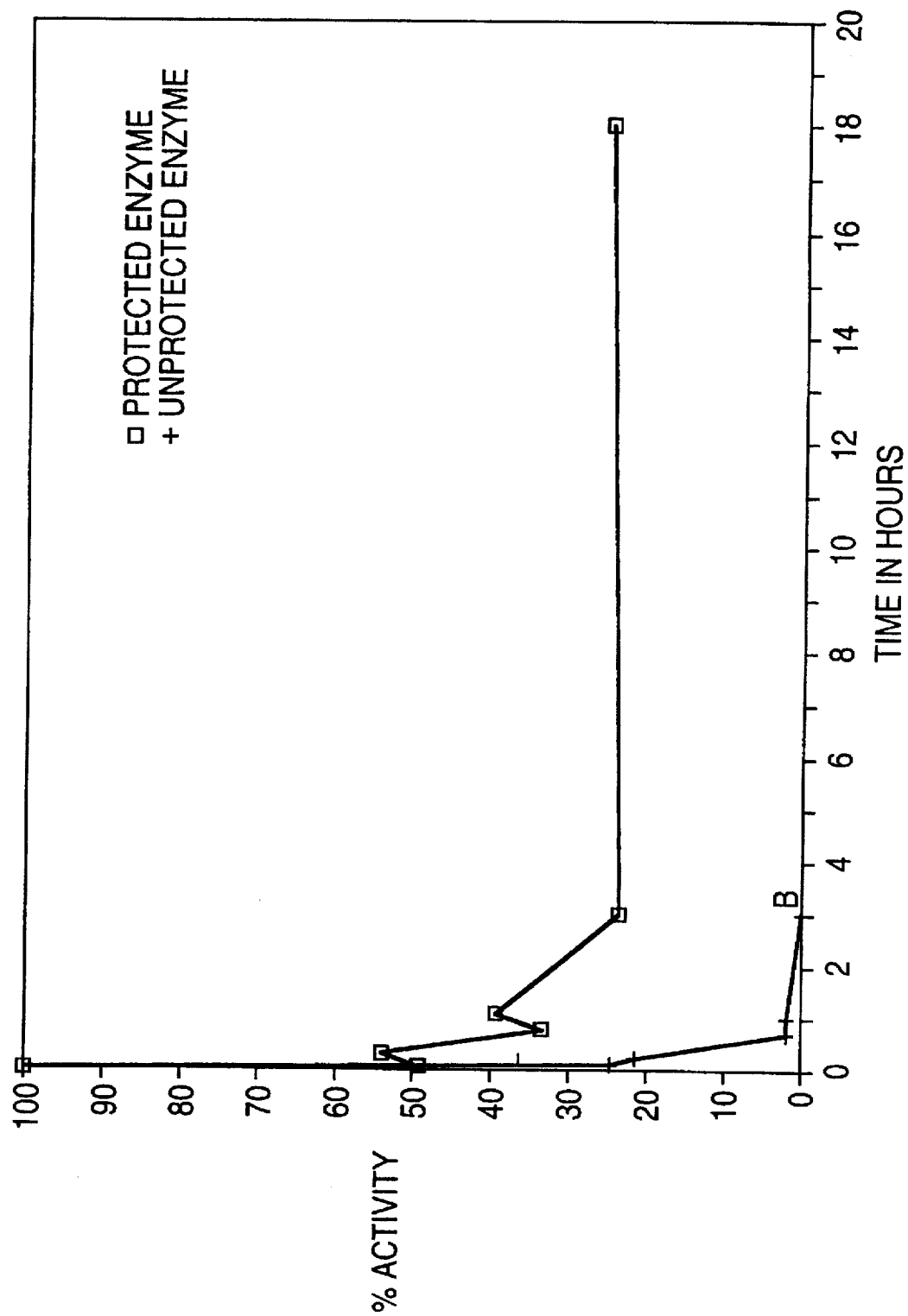
FIG. 5 is a graph depicting the loss of activity of asparaginase when that biologically active entity is subjected to pH 3.0 at 37° C. compared with the prolongation of activity displayed by protected enzyme, in accordance with this invention, under the same conditions.

The plot of L-asparaginase residual activity versus incubation time at pH 3 is shown in FIG. 5. Enzyme protected with a mixture of four MAbs retained over 30% of its activity after two hours, whereas the unprotected enzyme had less than 2% of its activity after only 45 minutes.

EXAMPLE 4

Protection of Trypsin Against Self-Digestion

Rabbit polyclonal anti-trypsin serum was obtained from Ventrex Laboratories (Portland, Me.). An IgG fraction was purified from the serum by the use of a MAPS II protein A kit (product of Bio-Rad Laboratories, Richmond, Calif.). The purified IgG fraction was dialyzed against 0.1M Tris-HCl (pH 8.0), with several changes of buffer. The final protein concentration of the resulting antibody solution was 800 mg/ml and, with an assumed content of 5% for IgG specific for trypsin, the concentration of specific antibody was 40 mg/ml.

To 20 ml of trypsin solution (20 units; 2 mg) in the same Tris-HCL buffer were added 315 ml (12.6 mg of specific IgG; 252 mg of total IgG) of antibody solution to give a 1:1 molar ratio of trypsin to specific IgG. Water (65 ml) was added to give a final trypsin concentration of 50 units/ml.

Two controls were prepared, one containing 252 mg of bovine serum albumin and the other containing no protein. Final trypsin concentration were also 50 units per ml.

All samples were incubated at 4° C., and 50 ml of each were assayed for trypsin activity at 0, 1, 3, 5 and 6 days by means of the above-mentioned Gilford spectrophotometer (temperature: 25° C.; absorbance at 247 nm). The linear rate constant for each sample were then determined and the residual activity calculated as described in Example 3.

Figure 6:
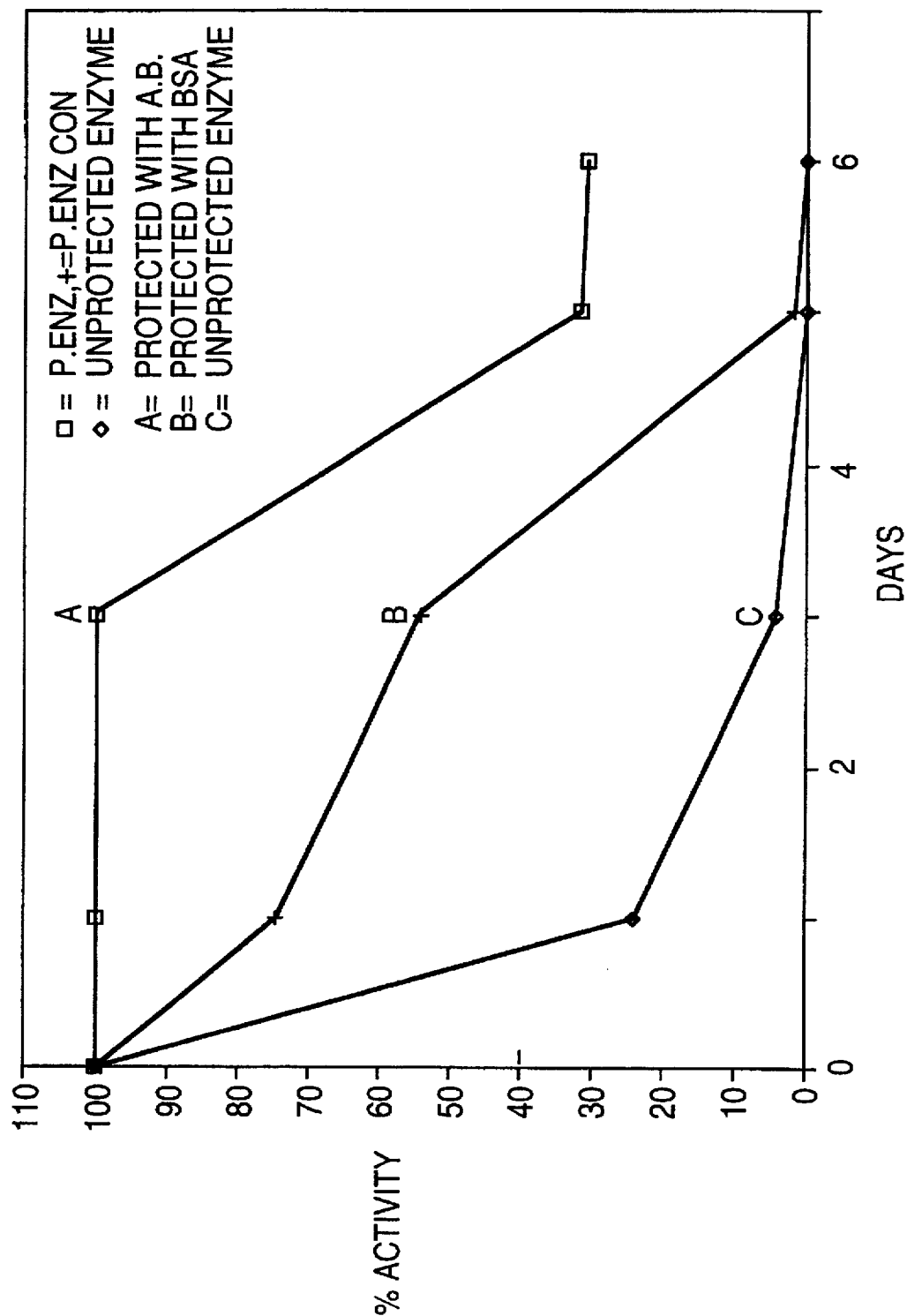
FIG. 6 demonstrates graphically the loss of activity due to self-destruction over time of a biologically-active entity (trypsin) compared with trypsin protected in accordance with the present invention.

Trypsin protected with a rabbit anti-trypsin polyclonal antibody maintained 100% of its activity for up to three days,. whereas unprotected trypsin lost 75% of its activity after one day, at 4° C. As shown in FIG. 6, where percentage activity is plotted against time (days), when nonspecific protein (BSA) was added to trypsin, there was a 50% protection of its activity after 3 days, but this protection was significantly lower than that associated with the antibody. Moreover, the protection achieved with BSA went down to near-zero after five days, while 30% protection was maintained after six days when antibody was used.

EXAMPLE 5

Protection of Subtilisin Against Inactivation by an Oxidizing Agent

Subtilisin-antibody complex was prepared as in Example 3. An unprotected control was prepared by adding 1.25 mg of subtilisin (EC 3.4.21.14; Boehringer Mannheim catalog No. 165905) to 136 mg of BSA in 1.5 ml of 50 mM KCl and 50 mM Tris-HCl buffer (pH 8.0). A 0.5 mM solution of the enzyme substrate, N-succinyl-ala-ala-pro-phe p-nitroanilide, was prepared in 0.1M Tris-HCl buffer (pH 7.8). A commercial bleach formulation (JAVEX), containing 6% sodium hypochlorite, was used as the oxidizing agent.

Samples of subtilisin protected with mouse anti-subtilisin polyclonal antibody and of unprotected subtilisin, respectively, were subjected to increasing concentrations of sodium hypochlorite at 37° C. for 15 minutes. Substrate was then added to each sample and the activity of the enzyme determined, at 37° C., by monitoring an increase in absorbance at 410 nm which was correlated with the rate of hydrolysis of the substrate.

Figure 7:
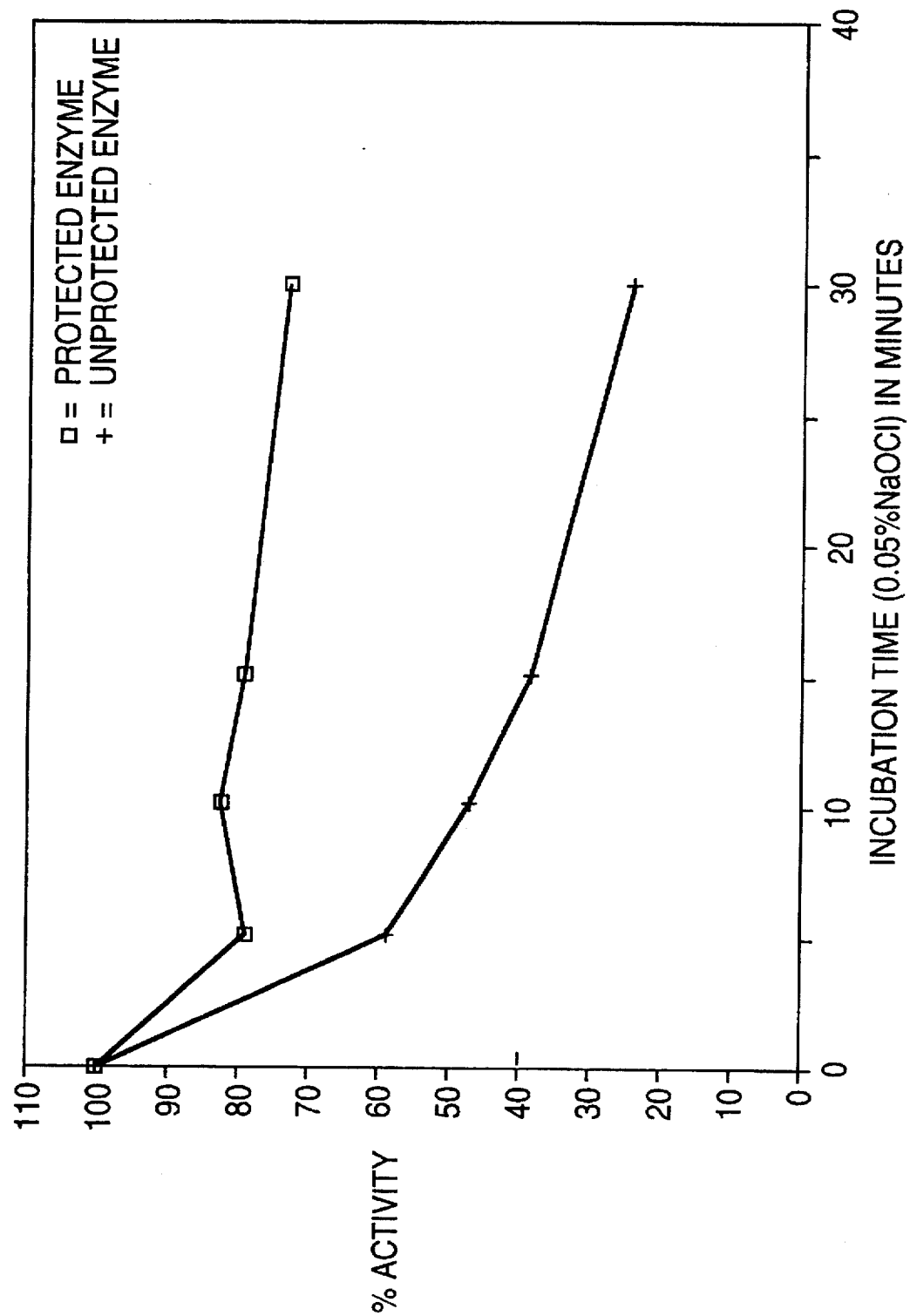
FIG. 7 is a graph showing the loss of activity by another biologically active entity, subtilisin, in the presence of 0.05% NaOCl, compared with the same entity protected in accordance with this invention.

In the oxidant-concentration range of 0.04% to 0.15%, the protected enzyme was at least twice as active as the unprotected enzyme. By the same token, it was found that the protected subtilisin, when exposed to 0.05% of sodium hypochlorite for various times, retained its activity longer than unprotected enzyme subjected to the same conditions (see FIG. 7). After 30 minutes preincubation with 0.05% sodium hypochlorite, for example, the protected subtilisin retained over 75% of original activity, whereas the unprotected subtilisin displayed less than 25% of original activity.

EXAMPLE 6

Protection of Glucoamylase Against the Effect of Alcohol

Glucoamylase (DIAZYME L-200; product of Miles Laboratories) protected with rabbit anti-glucoamylase polyclonal antibody was prepared in accordance with Example 5. Sets of three samples each of the enzyme-antibody complex and unprotected glucoamylase plus non-immune human IgG were exposed, respectively, to no alcohol, 2.5% ethanol and 5% ethanol (v/v). The samples were incubated for various times at 37° C. before being assayed for enzyme activity.

Figure 8:
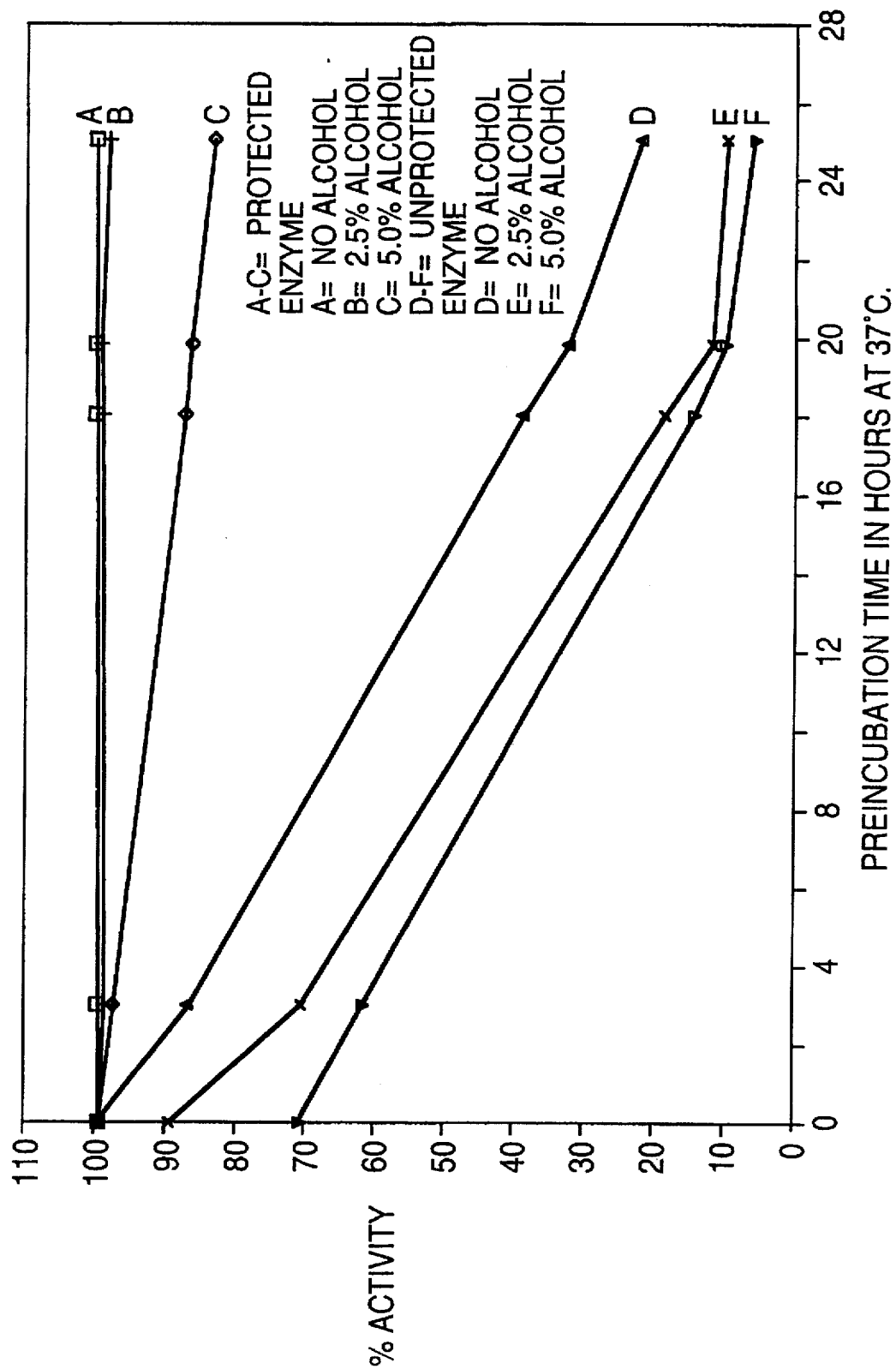
FIG. 8 is a graph demonstration of the loss of activity of glucoamylase when that biologically active entity is exposed to increases in alcohol concentration, compared with the same entity protected in accordance with the invention.

The results are illustrated in FIG. 8. Unprotected enzyme samples exposed to 2.5% and 5% ethanol lost 50% of activity in 8 and 10 hours, respectively. Protected samples, by contrast, suffered an average loss of less than 5% of original activities after 10 hours.

EXAMPLE 7

Generation of Chimeric Protein Comprising L-Asparaginase and an L-Asparagrinase-Specific Single Chain Antibody and Evaluation of its Resistance to Inactivation by Trypsin.

1. OLIGONUCLEOTIDE SYNTHESIS 1.1. Oligonucleotide Primers

All oligonucleotide primers were synthesized on a Waters DNA synthesizer. Primers used for PCR isolation and cloning of the mouse immunoglobulin light-chain and heavy-chain variable regions are listed in Table 2 (SEQ ID NOS 1–4). Light chain primers were based on those published by LeBoeuf et al., *Gene* 82:371–377 (1989) and heavy chain primers were based on those published by Coloma et al., *Biotechniques* 11:152–156 (1991). Primers used for PCR isolation and cloning of the L-asparaginase II (ansB) gene were based on the sequence published by Jennings and Beacham, *J. Bacteriol.* 172:1491–1498 (1990) and are described in Table 3 (SEQ ID NOS 5 and 6). Primers used for the two step PCR assembly of the "Single Chain Antibody" (SCA) portion of the chimeric gene are listed in Table 4 (SEQ ID NOS 7–10). The internal primers contain nucleotide sequences which code for the flexible linker $(Gly_4Ser)_3$ according to Huston et al., *Proc. Natl. Acad. Sci. USA* 85:5879–5883 (1988).

TABLE 2

Primers for cloning of IgG sequences

Light Chain 5' Sense Primer (SEQ ID NO: 1)

| 5'GGT CGA CCG | ACA | TCG | TCC | TCA | CAC | AAT | CIC | CAG-3' |
|---|---|---|---|---|---|---|---|---|
| SalI | T | T | G | G | C | G | | |
| | | | | T | T | | | |

Light Chain 3' Constant Region Antisense Primer (SEQ ID NO: 2)

| 5'GGT CGA CCT | GGT | GGG | AAG | ATG | G-3' |
|---|---|---|---|---|---|
| SalI | | | | | |

Heavy Chain 5' Sense Primer (SEQ ID NO: 3)

| 5'-TAC GGA TCC | GAG | GTC | AAA | CTG | CAG | CAG | TCT-3' |
|---|---|---|---|---|---|---|---|
| BamHI | C | G C G | | | | | |

Heavy Chain 3' Constant Region Antisense Primer (SEQ ID NO: 4)

| 5'-TAG GAA TTC | ATC | TCC | ACA | CAC | AGG | AAC | CAG | TGG | ATA | GAC-3' |
|---|---|---|---|---|---|---|---|---|---|---|
| EcoRI | C | | | | | GG | | | | |

TABLE 3

Primers for cloning of asparaginase II gene ansB 5' Sense Primer (SEQ ID NO: 5)

| 5'-GCC GGA TCC | TTA | CCC | AAT | ATC | ACC | ATT-3' |
|---|---|---|---|---|---|---|
| BamHI | | | | | | | ansB 3' Antisense Primer (SEQ ID NO: 6)

| 5'-GGC TCT AGA | GCG | AGG | CGA | TTA | GTA | CTG-3' |
|---|---|---|---|---|---|---|
| XbaI | | | | | | |

TABLE 4

Primers for assembly of single chain antibody

$V_L$ 5' Sense Primer (SEQ ID NO: 7)

5'-CGC <u>GGA TCC</u> GAT ATT GTC CTC ACT CAA-3'
    BamHI $V_L$ 3' Antisense Internal Primer (SEQ ID NO: 8)

5'AGA TCC GCC GCC ACC CGA CCC ACC ACC GCC CGA GCC ACC
GCC ACC TGG GAA GAT GGA TAC-3'

$V_H$ 5' Sense Internal Primer (SEQ ID NO: 9)

5'-GGT GGC GGT GGC TCG GGC GGT GGT GGG TCG GGT GGC GGC
GGA TCT CAG GTC AAG CTG CAG-3'

$V_H$ 3' Antisense Primer (SEQ ID NO: 10)

5'-TCT CT<u>A GAT C</u>TC CAC ACA CAG GAG
    XbaI

1.2. Oligonucleotides used for the 2X Linker

The complementary 96-mer oligonucleotides used to construct the 2x linker, shown in Table 5, were synthesized on an Applied Biosystems Model 380A DNA synthesizer. Oligonucleotides were purified on a Nap 5 column (Pharmacia) according to the manufacturer's recommended protocol. These complementary oligonucleotides were comprised of nucleic acid sequences encoding six repeats of the Gly$_4$Ser amino acid sequence. Thus, the resulting linker was twice as long as the linker used in the single chain antibody portion of the chimeric gene.

TABLE 5

2X Linker Oligonucleotides

2X Linker Sense Oligonucleotide (SEQ ID NO: 11)

5'-<u>CTA GAG</u> GTG GCG GTG GCT CGG GCG GTG GTG GGT CGG GTG
GCG GCG
    GAT CTG GTG GCG GTG GCT CGG GCG GTG GTG GGT CGG GTG
GCG GCG
    GAT CTA-3'

2X Linker Antisense Oligonucleotide (SEQ ID NO: 12)

5'-<u>GAT CTA</u> GAT CCG CCG CCA CCC GAC CCA CCA CCG CCC GAG
CCA CCG
    CCA CCA GAT CCG CCG CCA CCC GAC CCA CCA CCG CCC GAG
CCA CCG
    CCA CCT-3'

2. CELL LINE

The mouse hybridoma cell line used (clone #12) was previously shown to secrete a monoclonal antibody (IgG$_{2b}$) subclass which recognizes *E. coli* L-asparaginase II and protects L-asparaginase against inactivation by trypsin. EPA Publication No. EP 0 298 654 A2; Ramjeesingh et al., *BIO/TECHNOLOGY* 10:442–445, (1992).

An ampule of the cell line producing monoclonal antibody (MAb) #12, was retrieved from Liquid N$_2$, thawed quickly by immersing in 37° C. water bath, transferred to 15 ml sterile conical tubes containing 5 mls of warm (37° C.) medium (Dulbecco H-21, 10% fetal calf serum, 50 IU/ml Penicillin and 50 µg/ml Streptomycin) and spun down at 250 g for 5 minutes to pellet the cells. The supernatant was discarded and cells were resuspended in 15 ml of fresh medium (as above) in Petri dishes that were placed in a humidified CO$_2$ incubator set at 6% CO$_2$ and 37° C. After three days in culture, the cells were diluted 1:10 in fresh medium and transferred to ten petri dishes each containing 20 ml of fresh medium. When the cells reached a density of 1×10$^6$ cells per ml, the medium was collected and transferred to four 50 ml tubes and spun down at 500 g for 10 minutes. The supernatant was discarded and pelleted cells were transferred into freezing vials and stored in liquid N$_2$ until used.

3. ISOLATION AND CLONING OF THE LIGHT AND HEAVY CHAIN VARIABLE REGIONS

3.1. Preparation of RNA

RNA was extracted from hybridoma cells using the acid guanidinium-phenol-chloroform method of Chomczynski and Sacchi, *Anal. Biochem.* 162:156–159 (1987). Approximately 200 mg of pelleted cells was used as starting material. Poly(A)$^+$ RNA was isolated from the total RNA using the Poly(A) QUIK mRNA isolation kit (Stratagene, La Jolla, Calif.).

3.2. Isolation and Cloning of the Light and Heavy Chain Variable Regions

3.2.1. First Strand Synthesis

One µg of purified mRNA was combined with 50 pmol of either the light chain or heavy chain constant region antisense primers (Table 2), 200 U reverse transcriptase, 20 U RNase inhibitor (RNASIN, Promega), 2 µl 10 mM dNTPs and 2 µl 10X PCR buffer in a final volume of 20 µl. The mRNA and primers were preheated to 90° C. for 5 minutes and then quick-chilled on ice before addition to the rest of the reaction mixture. The final reaction mixture was then incubated at 23° C. for 10 minutes, followed by incubation at 42° C. for 60 minutes. After completing first strand syntheses, the reaction mixtures were heated to 95° C. for 5 minutes, spun down and quick-chilled on ice in preparation for PCR.

3.2.2. PCR of the Light and Heavy Chain Variable Regions

Polymerase chain reaction (PCR) mixtures of 80 μl were added to the completed first strand syntheses (20 μl) such that the final reaction mixtures (100 μl) contained 1X PCR buffer, 50 pmol antisense, light-chain 3'-constant region primer (or antisense, heavy-chain 3'-constant region primer), 50 pmol sense, light-chain 5'-degenerate primer (or sense, heavy-chain 5'-degenerate primer) (Table 2) and 2 units Taq polymerase. Both light chain primers were phosphorylated to facilitate blunt-end cloning. Reaction mixtures were overlaid with 100 μl of mineral oil. PCR was performed on the Perkin Elmer Cetus Gene Amp PCR System 9600 thermocycler. PCR profiles consisted of 1 minute denaturation at 94° C., 2 minutes annealing at 50° C. (52° C. for heavy chain samples) and 3 minutes extension at 72° C. The cycles were repeated 24 times followed by a final cycle with a 5 minutes extension at 72° C.

3.2.3. Cloning of Mouse Immunoglobulin Light and Heavy Chain Variable regions "Gel Purifaction" was used to purify light chain PCR products after electrophoresis in 1% low melting point agarose. The excised gel slice containing the light chain variable region DNA fragment was melted at 65° C. and DNA was extracted twice with phenol, once with phenol:chloroform:isoamyl alcohol (25:24:1) and once with chloroform:isoamyl alcohol (24:1), followed by ethanol precipitation. The ends of the fragment then were filled in using Klenow fragment (Bethesda Research Laboratories, Bethesda, Maryland). DNA was extracted once with phenol:chloroform (24:1) and once with chloroform:isoamyl alcohol (24:1), followed by ethanol precipitation. The light chain variable region DNA fragment was then blunt-end ligated into an EcoRV-cut, alkaline phosphatase-treated plasmid pBluII KS (Stratagene, La Jolla, Calif.). The plasmid vector had previously been prepared by digestion with EcoRV, treated with alkaline phosphatase followed by gel purification (as described above).

Heavy chain PCR products were extracted once with phenol:chloroform:isoamyl alcohol (25:24:1) and once with chloroform:isoamyl alcohol (24:1), followed by ethanol precipitation. The PCR products were then digested with BamHI and EcoRI. The digested heavy chain DNA was gel purified as previously described and the heavy chain variable region DNA fragment was ligated into the BamHI and EcoRI restriction sites in the polylinker of the plasmid vector pBluII SK⁻. The plasmid vector was previously prepared by digestion with BamHI and EcoRI followed by gel purification (see above).

All light and heavy chain ligation products were transformed into *E. coli* DH5a using standard procedures. Maniatis et al., In *MOLECULAR CLONING*, p. 250, Cold Spring Laboratory Press (1982). Transformants were screened and selected on agar plates containing ampicillin, using blue/white color selection coupled with restriction analysis of plasmid mini-preps prepared by alkali lysis. Mantiatis et al., supra at p. 368–369. Clones were verified by sequence analysis and by comparison to other mouse immunoglobulin sequences published in GenBank. Recombinant plasmids found to contain either the light or heavy chain variable regions were designated pBluLC and pBluHC, respectively. FIGS. 9 and 10, SEQ ID NOS 13 and 14.

3.2.4. Assembly of the Light and Heavy Chain Variable Region Fragments into a Single Chain Antibody (SCA) Sequence The complete SCA portion of the chimeric gene was constructed in a manner analogous to the protocols originally published by Huston et al., *Proc. Nat'l Acad. Sci. USA* 85:5879–5883 (1988) and Bird et al., *Science* 242:423–426 (1988). Instead of ligating numerous synthetic oligonucleotides to form the chimeric SCA sequence, however, a simpler, more rapid two-step PCR procedure, based on the protocol of Davis et al., *BIO/TECHNOLOGY* 9:165–169 (1991), was used for the assembly process. The initial PCR reaction mixture (100 μl) contained 10 ng of pBluLC, 10 ng pBluHC, 50 pmol $V_L$ 5' sense primer, 50 pmol $V_L$ 3' antisense internal primer, 50 pmol $V_H$ 5' sense internal primer, 50 pmol $V_H$ 3' antisense primer (Table 4), 200 μM dNTPs, 1X PCR buffer, and 2.5 U Taq polymerase. The PCR cycle profiles were as follows: 1 cycle of 2 minutes denaturation at 94° C., 1 minute annealing at 60° C., and 1 minute extension at 72° C.; 23 cycles of 30 s denaturation at 94° C., 1 minute annealing at 60° C., 1 minute extension at 72° C.; 1 cycle of denaturation at 94° C., 1 minute annealing at 60° C. and a 5 minutes extension at 72° C. After the first round (25 cycles) of amplification, 10 μl of the first PCR reaction mixture was combined with a second PCR reaction mixture comprising 50 pmol of $V_L$ 5' sense primer, 50 pmol of $V_H$ 3' antisense primer (Table 4), 200 μM dNTPs, 1X PCR buffer and 2.5 U of fresh Taq polymerase. The addition of only distal primers in the second PCR favored amplification of the complete SCA sequence. The second PCR reaction mixture was then subjected to another 25 cycles of amplification identical to those of the first round. Single chain antibody PCR products were extracted as described previously and ethanol precipitated. The single chain antibody DNA fragment was digested with BamHI and XbaI, gel purified, and ligated (T4 DNA Ligase; Bethesda Research Laboratories, Bethesda, Md.) into prepared plasmid vector pBluII KS⁻. Ligation products were transformed into the Dam⁻ host *E. coli* MO1 using standard procedures. Maniatis et al., supra at p. 250. Correct assembly of the single chain antibody was verified by restriction enzyme analysis of plasmid mini-preps (alkali lysis) and by sequence analysis. The new recombinant plasmid was referred to as pBluSCA.

4. ISOLATION, AMPLIFICATION AND CLONING OF THE *E. coli* ENZYME

L-Asparaginase (EC 3.5.1.1.) II (ansB) GENE

To obtain template starting material, genomic DNA was isolated from *E. coli* DH5a according to the procedure of Federoff et al., *J. Mol. Appl. Genet.* 2:11–24 (1983). The PCR reaction mixture (10 μl) for amplifying the ansB gene comprised the following components: 1 ng genomic DNA of *E. coli* DH5a, 25 pmol ansB 5' sense primer, 25 pmol ansB 3' antisense primer, 200 μM dNTPs, 1X PCR buffer and 2.5 U Taq polymerase. The PCR cycle profiles were as follows: 24 cycles of 1.5 minutes denaturation at 94° C., 1 minute annealing at 50° C. and 1.5 minutes extension at 72° C. A final cycle with a 5 minute extension at 72° C. was performed to facilitate complete synthesis. The ansB PCR products were extracted as described previously and ethanol precipitated. The ansB DNA fragment was digested with BamHI and XbaI, gel purified and ligated into the plasmid vector pBluII KS⁻. The vector had been digested with BamHI and XbaI and gel purified. Ligation products were transformed into *E. coli* DH5a using standard procedures. For example, Maniatis et al., supra at p. 250. Transformants were chosen on the basis of blue/white color selection. Amplification of the ansB gene was confirmed by restriction enzyme analysis of plasmid mini-preps (alkali lysis) and by full sequence analysis. The recombinant plasmid was designated as pBluansB.

5. FINAL ASSEMBLY OF THE FULL CHIMERIC GENE

5.1. Preparation of ansB

In order to assemble the complete chimeric gene, it was necessary to eliminate the XbaI restriction site at the 3' end of the ansB gene. Therefore, pBluansB was digested with XbaI, the ends were filled in using Klenow, and a phosphorylated EcoRI adaptor (Promega, Madison, Wis.) was ligated onto the ends. The linearized plasmid containing the new construct was then digested with BamHI to release the ansB gene now possessing an EcoRI restriction site on its 3' end. This new ansB fragment was gel purified and ligated into pTZ18u (US Biolabs, Chicago, Ill.) at the BamHI and EcoRI restriction sites in the polylinker. Ligation products were transformed into E. coli DH5a and transformants selected. The new recombinant plasmid was referred to as pTZansB. The presence of the EcoRI adaptor on the 3' end of the ansB gene was confirmed by restriction analysis. All further assembly was done using this recombinant plasmid.

5.2. Addition of the 2X Flexible Linker

A 2X linker was formed by annealing two complementary 96-mer oligonucleotides using standard procedures. The annealed oligonucleotides possessed a fully functional XbaI site on the 5' end with respect to the sense strand. The 3' end had the same four base overhang as BamHI digested ends, but once ligated would not remake a cleavable BamHI site. This was accomplished by intentionally changing the first base upstream from the overhang from a G to an A, thus nullifying the BamHI site. The annealed nucleotides were ligated into previously prepared pTZansB at the XbaI and BamHI sites. Ligation products were transformed into E. coli DH5a. The new recombinant plasmid was designated pTZ2xLansB. Correct assembly was confirmed by sequence analysis.

5.3. Addition of the SCA Fragment to Complete the Full Chimeric Gene

The SCA sequence present in pBluSCA was excised by digestion with HindIII and XbaI, gel purified, and ligated into pTZ2xLansB. Ligation products were transformed into E. coli DH5a. The resulting recombinant plasmid, containing the full chimeric construct, was designated pTZFC (FC="full construct). This plasmid was analyzed for correctness by restriction and sequence analysis. See FIG. 11, SEQ ID NO:15.

5.4. Cloning of the Full Construct into the Expression Vector

Figure 12:
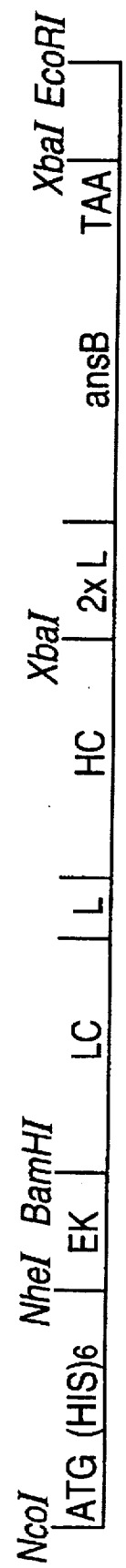
FIG. 12 is the map of the full construct for the expression of the chimeric protein. The chimeric protein gene was assembled in the vector pTrcHisA (Invitrogen—San Diego, Calif.) using the restriction enzymes BamHI and EcoRI. ATG—translation initiation site; (HIS)$_6$—six histidine codons used for the purification of the protein; EK—sequence that codes for the enterokinase specific cleavage site; LC—light chain variable region; L—linker region between light and heavy chains ((Gly$_4$Ser)$_3$); HC—heavy chain variable region; HC—heavy chain variable region; 2xL—linker region between the single chain antibody and the asparaginase protein ((Gly$_4$Ser)$_6$); ansB—asparaginase II coding sequence; TAA—translation stop codon; NcoI, NheI, BamHI, XbaI, EcoRI—restriction cleavage sites.

The full construct was excised from pTZFC by digestion with BamHI and EcoRI, gel purified and ligated into the polyhistidine expression vector pTrcHisA (Invitrogen, La Jolla, Calf.) and ligation products were then transformed into E. coli SP9301. Transformants were verified by restriction analysis. The final recombinant plasmid was designated pTrcHisFC. The full chimeric gene is depicted in FIG. 12.

6. SCALE-UP EXPRESSION OF THE CHIMERIC PROTEIN

E. coli transformed with pTrcHisA-FC, grown on a solid LB mediumplate (1.5% Agar, 1% Tryptone, 0.5% Yeast Extract, 1% NaCl, 50 µg Ampicillin, pH 7.0), was used to inoculate a flask containing 100 ml of LB liquid medium (1% Tryptone, 0.5% Yeast Extract, 1% NaCl, 50 µg Ampicillin, pH 7.0). The bacterial culture was placed in a shaking incubator for overnight at 37° C. The following morning, the 600 nm O.D. of the culture was recorded (O.D. of 2.23). A second inoculation into 900 ml of LB medium was made so that the initial O.D. was above 0.1 (actual O.D. of 0.1134) and the second culture was incubated under the same conditions. After two hours, an O.D. of 0.39 was recorded (the target was between 0.3–0.4). Ten ml of IPTG (isopropylthio-β-D-galactoside MW 238.3) was added and the culture was placed back into the incubator for additional 5 hours under the same conditions. The culture was then spun down in a Sorvall™ RC2-B centrifuge at 7,000 RPM for 20 minutes. The supernatant was discarded and the pellet was pooled and resuspended in 20 ml of cold PBS (145 mM NaCl, 7.5 mM $Na_2HPO_4$, 2.5 mM $Na_2PO_4:2H_2$), pH 7.2). The resuspended sample was spun again in a Sorvall RC-5R centrifuge for 10 minutes at 5,000 RPM. This supernatant was discarded, the pellet resuspended in 5 ml of cold PBS, aliquotted into 5 microfuge tubes and spun down in an Eppendorf™ microfuge for 5 minutes at 10,000 g. This supernatant was discarded and pellets stored in the tubes at −70° C. until used.

7. PURIFICATION AND REFOLDING OF THE CHIMERIC PROTEIN

7.1. Purification of PolyHis-FC Expressed in E. coli SP9301 with Construct pTrc His A-Fc

7.1.1 Lysis and Solubilization

Bacterial pellets (five) prepared from 1 liter of growth media were pooled and resuspended in 20 mls of 20 mM phosphate, 500 mM sodium chloride containing 5µg per ml each of aprotinin and leupeptin, and 2 mM benzamide. Lysozyme (100 µg per ml) was added to the suspension followed by incubation on ice for 15 minutes. The bacterial suspension was freeze-thawed twice, aliquotted into microfuge tubes and spun down in an Eppendorf™ microfuge for 10 minutes at 10,000×g. The supernatant was collected and stored on ice. The pellets were resuspended and further treated with 20 mls of 6M guanidine, 20 mM phosphate and 500 mM NaCl, pH 7.8, and mechanically shaken for 20 minutes. Another microcentrifugation was performed as described above and the supernatant pooled with that from the first spin.

7.1.2. Purification

The chimeric protein was purified from the supernatant using an "XPRESS SYSTEM" kit (INVITROGEN CORP.) for the expression and purification of polyhistidine-containing recombinant protein. Briefly, a ProBond™ disposable column (INVITROGEN CORP.) was prepared per the manufacturer's instructions for the purification under denaturing conditions. The supernatant was applied to the column and allowed to flow under gravity at room temperature. The column was washed with 20 mls of binding buffer (8M urea, 20 mM sodium phosphate, 500 mM sodium chloride, pH 7.8), followed by 30 mls of wash buffer (8M urea, 20 mM sodium phosphate, 500 mM sodium chloride, pH 6.0). Bound protein was eluted from the column with the elution buffer (8M urea, 20 mM sodium phosphate, 500 mM sodium chloride, pH 4.0). This procedure yielded approximately 5 mg of purified protein.

7.2. Refolding

Purified chimeric protein (2 mg) in 5 mls of 20 mM phosphate, 500 mM NaCl, 8M urea, with a pH readjusted to 7.4, was dialyzed (Spectrapor dialysis tubing, MW cutoff 12 kD) at 4° C., against 1 liter of Buffer A (20 mM Tris, 2.5 mM calcium chloride, 100 mM sodium chloride and 0.1% mercaptoethanol, pH 7.4) containing 4M urea for 48 hours. The dialysis buffer was changed every 24 hours with each successive change containing decreasing concentrations of urea in 1 liter of Buffer A; 2M urea, 1M urea, 0.5M urea and 0.25M urea). Finally, four liters of Buffer A containing no urea was used. After the final dialysis step, aggregated protein was spun down for 10 minutes in a microfuge at 10,000×g, the supernatant was treated with thrombin (2 μg per ml) and incubated at room temperature for 15 minutes. The thrombin-treated sample was then dialyzed for 5 days at 4° C. against 4 liters of Buffer B (20 mM sodium borate, 100 mM sodium chloride, 1% glycerol and 0.05% sodium azide, pH 8.0). The refolded protein sample was finally dialyzed against four liters of Buffer C (20 mM sodium borate, 50 mM sodium chloride, pH 9.0 ) for 24 hours before measurement of asparaginase activity.

8. TESTING THE CHIMERIC PROTEIN FOR L-Asparaginase ACTIVITY AND ITS RESISTANCE TO INACTIVATION BY TRYPSIN IN COMPARISON TO THE NATIVE L-Asparaginase.

The method of Howard and Carpenter as summarized by Jayaram et al., *Analytical Biochemistry* 59:327–346 (1974) was used to measure asparaginase activity. In short, a Gilford spectrophotometer was used to monitor the conversion of L-asparagine to L-aspartic acid at 37° C. at 197 nm, employing borate buffer as a reference. Samples of the refolded enzyme (5 μl to 100 μl) in a semi-final volume of 250 μl of 5 mM borate buffer, pH 9.0, were added to an equal volume of 2 mM of L-asparagine in 5 mM borate buffer, pH 9.0 to give a final substrate concentration of 1 mM in 500 μl (500 nmoles).

To test the effect of trypsin on the chimeric protein, a sample of the refolded protein (50 μl, 0.002 unit) was diluted to a final volume of 250 μl of 5 mM borate buffer, pH 9.0 and added to an equal volume of 2 mM of L-asparagine in 5 mM borate, pH 9.0. Trypsin (250 units, 10 μl in water) were added and the rates of conversion of L-asparagine to L-aspartic acid measured. Trypsin treatment of L-asparaginase (EC 3.5.1.1) (SIGMA-A3809) of equivalent enzyme activity in the same volume of borate buffer was used for comparison.

Enzyme activity was determined as follows:

1. A conversion factor (mO.D. decrease per nmole of substrate consumed) was determined for each sample as follows. The maximum decrease in O.D. at 197 nm for different samples and controls was determined by adding 0.3 units of high specific activity (300 U/mg) of commercial preparation of L-asparaginase (SIGMA-A3809) to the different samples; for samples that were to contain trypsin, the O.D. was determined after trypsin was added and after all substrate (500 nmoles) was consumed. The measured O.D. drop at 197 nm was converted to mO.D. and the corresponding ratio of mO.D. to nmole substrate was calculated by dividing by 500 (total initial substrate present is 500 nmoles).

2. For each sample, the decrease in absorbance at 197 nm (from its initial level) was recorded at short time intervals (0.25 minutes) and converted to nmoles by dividing by the appropriate conversion factor (mO.D./nmole substrate).

3. The amount of substrate consumed in nmoles, as a function of time, was then plotted. The rate was determined from the slope of the resulting linear regression.

Enzyme activity is expressed inn moles substrate consumed per minute. Control samples without trypsin are considered to have 100% activity.

9. RESULTS

Figure 13:
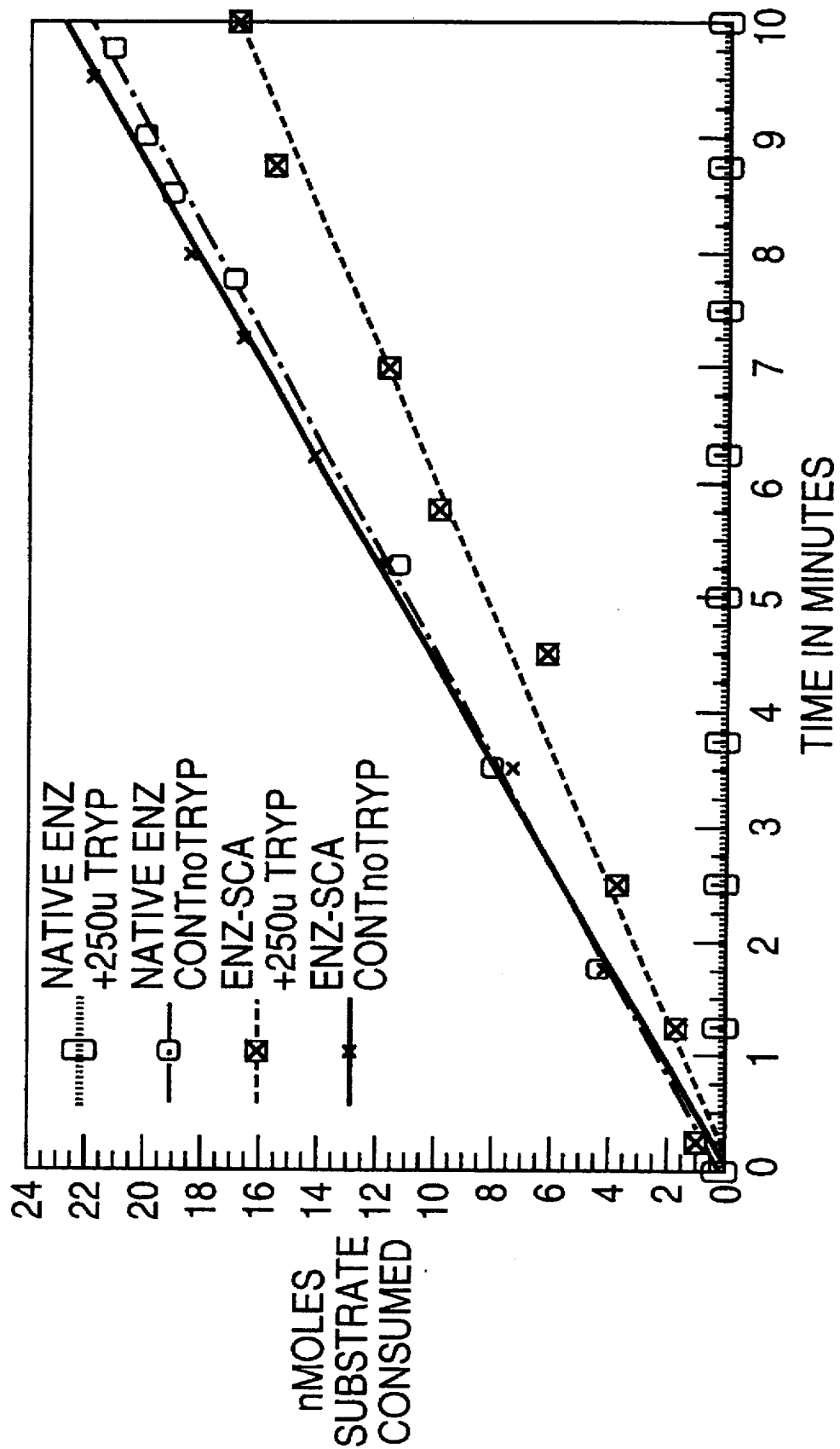
FIG. 13 is the chimeric protein resistance to trypsin inactivation. The graph depicts the consumption of substrate (L-asparagine) in nmoles by wild-type and chimeric L-Asparaginase in the absence and presence of trypsin (250 U/ml) as function of time.

While the wild-type L-asparaginase has lost all its activity after exposure to 250 U/ml of trypsin, the chimeric L-asparaginase containing a single chain version of MAb #12 has retained 75% of its original activity (see FIG. 13). This level of protection corresponds well with the protection afforded to wild-type L-asparaginase by free MAb #12 (72%) as we reported earlier. EPA Publication No. EP 0 298 654 A2; Ramjeesingh et al., *BIO/TECHNOLOGY* 10:442–445 (1992).

---

What is claimed is:

1. A recombinant, chimeric polypeptide chain comprising three distinct regions including a biologically active domain, a linker, and a single chain antibody wherein (i) the first region of said recombinant, chimeric polypeptide chain includes a biologically active domain and another domain which contains an epitope for binding to said single chain antibody;

(ii) the second region of said recombinant, chimeric polypeptide chain includes a single chain antibody having the light and heavy chains of an antibody variable region which specifically binds to said epitope in said first region of said recombinant, chimeric polypeptide chain;

(iii) and the third region of said recombinant, chimeric polypeptide chain includes a polypeptide linker connecting said first and second regions of said recombinant, chimeric polypeptide chain;

and wherein said recombinant chimeric polypeptide chain assumes a conformation wherein said single chain antibody is bound to said epitope of said first region and protects the biological activity of said first region of said recombinant, chimeric polypeptide chain;

and wherein binding to said epitope provides said biologically active domain with resistance to deactivation by a condition selected from the group consisting of denaturing temperature, denaturing pH, the presence of a proteolytic enzyme, the presence of an oxidizing agent, and the presence of alcohol;

and wherein said biologically active domain is selected from the group consisting of an enzyme, a hormone, a growth factor, and a polypeptide drug.

2. A continuous recombinant DNA sequence which encodes the recombinant chimeric polypeptide chain of claim 1.

3. A recombinant, chimeric polypeptide chain according to claim 1, wherein said biologically active domain corresponds to an enzyme.

4. A recombinant, chimeric polypeptide chain according to claim 1, wherein said biologically active domain corresponds to a hormone.

5. A recombinant, chimeric polypeptide chain according to claim 1, wherein said biologically active domain corresponds to a growth factor.

6. A recombinant, chimeric polypeptide chain according to claim 1, wherein said biologically active domain corresponds to a polypeptide drug.

7. The recombinant chimeric polypeptide of claim 1, wherein said deactivating condition is denaturing temperature.

8. The recombinant chimeric polypeptide of claim 1, wherein said deactivating condition is denaturing pH.

9. The recombinant chimeric polypeptide of claim 1, wherein said deactivating condition is the presence of a proteolytic enzyme.

10. The recombinant chimeric polypeptide of claim 1, wherein said deactivating condition is the presence of an oxidizing agent.

11. The recombinant chimeric polypeptide of claim 1, wherein said deactivating condition is the presence of alcohol.

* * * * *

UNITED STATES PATENT AND TRADEMARK OFFICE
CERTIFICATE OF CORRECTION

PATENT NO. : 5,686,579
DATED : November 11, 1997
INVENTOR(S) : SHAMI et al.

It is certified that error appears in the above-identified patent and that said Letters Patent is hereby corrected as shown below:

On title page,

In Section [54] Title: please delete in its entirety and insert --HALF-LIFE EXTENSION OF BIOLOGICALLY ACTIVE PROTEINS OR PEPTIDES THROUGH THE PRODUCTION OF CHIMERIC PROTEINS COMPRISING THE BIOLOGICALLY ACTIVE PROTEIN OR PEPTIDE AND A PROTECTIVE SINGLE-CHAIN ANTIBODY--.

Column 1, title, please delete in its entirety and insert --HALF-LIFE EXTENSION OF BIOLOGICALLY ACTIVE PROTEINS OR PEPTIDES THROUGH THE PRODUCTION OF CHIMERIC PROTEINS COMPRISING THE BIOLOGICALLY ACTIVE PROTEIN OR PEPTIDE AND A PROTECTIVE SINGLE-CHAIN ANTIBODY--.

Signed and Sealed this

Twenty-fourth Day of March, 1998

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 29
    ( D ) OTHER INFORMATION: /mod_base=i ( x i ) SEQUENCE DESCRIPTION: SEQ ID NO:1:

GGTCGACCGA YATYGTSCTB ACHCARTCNC CAG         33

( 2 ) INFORMATION FOR SEQ ID NO:2:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i v ) ANTI-SENSE: YES ( x i ) SEQUENCE DESCRIPTION: SEQ ID NO:2:

GGTCGACCTG GTGGGAAGAT GG     22

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TACGGATCCS AGGTSMARCT GCAGCAGTCT     30

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:4:

TAGGAATTCA YCTCCACACA CAGGARSCAG TGGATAGAC     39

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GCCGGATCCT TACCCAATAT CACCATT     27

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:6:

GGCTCTAGAG CGAGGCGATT AGTACTG     27

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CGCGGATCCG ATATTGTCCT CACTCAA     27

( 2 ) INFORMATION FOR SEQ ID NO:8:

( i ) SEQUENCE CHARACTERISTICS:
        ( A ) LENGTH: 60 base pairs
        ( B ) TYPE: nucleic acid (C) STRANDEDNESS: single
(D) TOPOLOGY: linear (iv) ANTI-SENSE: YES (xi) SEQUENCE DESCRIPTION: SEQ ID NO:8:

AGATCCGCCG CCACCCGACC CACCACCGCC CGAGCCACCG CCACCTGGGA AGATGGATAC    60

(2) INFORMATION FOR SEQ ID NO:9:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (xi) SEQUENCE DESCRIPTION: SEQ ID NO:9:

GGTGGCGGTG GCTCGGGCGG TGGTGGGTCG GGTGGCGGCG GATCTCAGGT CAAGCTGCAG    60

(2) INFORMATION FOR SEQ ID NO:10:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (iv) ANTI-SENSE: YES (xi) SEQUENCE DESCRIPTION: SEQ ID NO:10:

TCTCTAGATC TCCACACACA GGAG    24

(2) INFORMATION FOR SEQ ID NO:11:

(i) SEQUENCE CHARACTERISTICS:
      (A) LENGTH: 96 base pairs
      (B) TYPE: nucleic acid
      (C) STRANDEDNESS: single
      (D) TOPOLOGY: linear (xi) SEQUENCE DESCRIPTION: SEQ ID NO:11:

CTAGAGGTGG CGGTGGCTCG GGCGGTGGTG GGTCGGGTGG CGGCGGATCT GGTGGCGGTG    60
GCTCGGGCGG TGGTGGGTCG GGTGGCGGCG GATCTA    96

(2) INFORMATION FOR SEQ ID NO:12:

(i) SEQUENCE CHARACTERISTICS:
      (A) LENGTH: 96 base pairs
      (B) TYPE: nucleic acid
      (C) STRANDEDNESS: single
      (D) TOPOLOGY: linear (iv) ANTI-SENSE: YES (xi) SEQUENCE DESCRIPTION: SEQ ID NO:12:

GATCTAGATC CGCCGCCACC CGACCCACCA CCGCCCGAGC CACCGCCACC AGATCCGCCG    60
CCACCCGACC CACCACCGCC CGAGCCACCG CCACCT    96

(2) INFORMATION FOR SEQ ID NO:13:

(i) SEQUENCE CHARACTERISTICS:
      (A) LENGTH: 360 base pairs
      (B) TYPE: nucleic acid
      (C) STRANDEDNESS: single
      (D) TOPOLOGY: linear (xi) SEQUENCE DESCRIPTION: SEQ ID NO:13:

| GATATTGTCC | TCACTCAATC | GCCAGCAATC | ATGTCTGCAT | CTCCAGGGGA | AAAGGTCACC | 60 |
| ATGACCTGCA | GGGCCAGCTC | AAGTGTAAGT | TCCAGTTACT | TGCACTGGTA | CCAGCAGAAG | 120 |
| TCAGGTGCCT | CCCCCAAACT | CTGGATTTAT | AGCACATCCA | ACTTGGCTTC | TGGAGTCCCT | 180 |
| GCTCGCTTCA | GTGGCAGTGG | GTCTGGGACC | TCTTACTCTC | TCACAATCAG | CAGTGTGGAG | 240 |
| GCTGAAGATG | CTGCCACTTA | TTACTGCCAG | CAGTACAGTG | GTTACCCACT | CACGTTCGGA | 300 |
| GGGGGGACCA | AGCTGGAAAT | AAAACGGGCT | GATGCTGCAC | CAACTGTATC | CATCTTCCCA | 360 |

( 2 ) INFORMATION FOR SEQ ID NO:14:

( i ) SEQUENCE CHARACTERISTICS:
( A ) LENGTH: 360 base pairs
( B ) TYPE: nucleic acid
( C ) STRANDEDNESS: single
( D ) TOPOLOGY: linear ( x i ) SEQUENCE DESCRIPTION: SEQ ID NO:14:

| CAGGTCAAGC | TGCAGGAGTC | TGGGGGAGGC | TTAGTGCAGC | CTGGAGGGTC | CCGGAAACTC | 60 |
| TCCTGTGCAG | CCTCTGGATT | CACTTTCAGT | AGCTTTGGAA | TGCACTGGGT | TCGTCAGGCT | 120 |
| CCAGAGAAGG | GGCTGGAGTG | GGTCGCATAC | ATTAGTAGTG | GCAGTAGTAC | CCTCCACTAT | 180 |
| GCAGACACAG | TGAAGGGCCG | ATTCACCATC | TCCAGAGACA | ATCCCAAGAA | CACCCTGTTC | 240 |
| CTGCAAATGA | ACTACCCTC | ACTATGCTAT | GGACTACTGG | GGTCAAGGAA | CCTCAGTCAC | 300 |
| CGTCTCCTCA | GCCAAAACGA | CACCCCCATC | TGTCTATCCA | CTGGCTCCTG | TGTGTGGAGA | 360 |

( 2 ) INFORMATION FOR SEQ ID NO:15:

( i ) SEQUENCE CHARACTERISTICS:
( A ) LENGTH: 1848 base pairs
( B ) TYPE: nucleic acid
( C ) STRANDEDNESS: single
( D ) TOPOLOGY: linear ( x i ) SEQUENCE DESCRIPTION: SEQ ID NO:15:

| GATATTGTCC | TCACTCAATC | GCCAGCAATC | ATGTCTGCAT | CTCCAGGGGA | AAAGGTCACC | 60 |
| ATGACCTGCA | GGGCCAGCTC | AAGTGTAAGT | TCCAGTTACT | TGCACTGGTA | CCAGCAGAAG | 120 |
| TCAGGTGCCT | CCCCCAAACT | CTGGATTTAT | AGCACATCCA | ACTTGGCTTC | TGGAGTCCCT | 180 |
| GCTCGCTTCA | GTGGCAGTGG | GTCTGGGACC | TCTTACTCTC | TCACAATCAG | CAGTGTGGAG | 240 |
| GCTGAAGATG | CTGCCACTTA | TTACTGCCAG | CAGTACAGTG | GTTACCCACT | CACGTTCGGA | 300 |
| GGGGGGACCA | AGCTGGAAAT | AAAACGGGCT | GATGCTGCAC | CAACTGTATC | CATCTTCCCA | 360 |
| GGTGGCGGTG | GCTCGGGCGG | TGGTGGGTCG | GGTGGCGGCG | GATCTCAGGT | CAAGCTGCAG | 420 |
| GAGTCTGGGG | GAGGCTTAGT | GCAGCCTGGA | GGGTCCCGGA | AACTCTCCTG | TGCAGCCTCT | 480 |
| GGATTCACTT | TCAGTAGCTT | TGGAATGCAC | TGGGTTCGTC | AGGCTCCAGA | GAAGGGGCTG | 540 |
| GAGTGGGTCG | CATACATTAG | TAGTGGCAGT | AGTACCCTCC | ACTATGCAGA | CACAGTGAAG | 600 |
| GGCCGATTCA | CCATCTCCAG | AGACAATCCC | AAGAACACCC | TGTTCCTGCA | AATGAAACTA | 660 |
| CCCTCACTAT | GCTATGGACT | ACTGGGGTCA | AGGAACCTCA | GTCACCGTCT | CCTCAGCCAA | 720 |
| AACGACACCC | CCATCTGTCT | ATCCACTGGC | TCCTGTGTGT | GGAGATCTAG | AGGTGGCGGT | 780 |
| GGCTCGGGCG | GTGGTGGGTC | GGGTGGCGGC | GGATCTGGTG | GCGGTGGCTC | GGGCGGTGGT | 840 |
| GGGTCGGGTG | GCGGCGGATC | TAGATCCTTA | CCCAATATCA | CCATTTTAGC | AACCGGCGGG | 900 |
| ACCATTGCCG | GTGGTGGTGA | CTCCGCAACC | AAATCTAACT | ACACAGTGGG | TAAAGTTGGC | 960 |
| GTAGAAAATC | TGGTTAATGC | GGTGCCGCAA | CTAAAAGACA | TTGCGAACGT | TAAAGGCGAG | 1020 |

-continued

| | | | | | | |
|---|---|---|---|---|---|---|
|CAGGTAGTGA|ATATCGGCTC|CCAGGACATG|AACGATAATG|TCTGGCTGAC|ACTGGCGAAA|1080|
|AAAATTAACA|CCGACTGCGA|TAAGACCGAC|GGCTTCGTCA|TTACCCACGG|TACCGACACG|1140|
|ATGGAAGAAA|CTGCTTACTT|CCTCGACCTG|ACGGTGAAAT|GCGACAAACC|GGTGGTGATG|1200|
|GTCGGCGCAA|TGCGTCCGTC|CACGTCTATG|AGCGCAGACG|GTCCATTCAA|CCTGTATAAC|1260|
|GCGGTAGTGA|CCGCAGCTGA|TAAAGCCTCC|GCCAACCGTG|GCGTGCTGGT|AGTGATGAAT|1320|
|GACACCGTGC|TTGATGGCCG|TGACGTCACC|AAAACCAACA|CCACCGACGT|AGCGACCTTC|1380|
|AAGTCTGTTA|ACTACGGTCC|TCTGGGTTAC|ATTCACAACG|GTAAGATTGA|CTACCAGCGT|1440|
|ACCCCGGCAC|GTAAGCATAC|CAGCGACACG|CCATTCGATG|TCTCTAAGCT|GAATGAACTG|1500|
|CCGAAAGTCG|GCATTGTTTA|TAACTACGCT|AACGCATCCG|ATCTTCCGGC|TAAAGCACTG|1560|
|GTAGATGCGG|GCTATGATGG|CATCGTTAGC|GCTGGTGTGG|GTAACGGCAA|CCTGTATAAA|1620|
|TCTGTGTTCG|ACACGCTGGC|GACCGCCGCG|AAAACCGGTA|CTGCAGTCGT|GCGTTCTTCC|1680|
|CGCGTACCGA|CGGGCGCTAC|CACTCAGGAT|GCCGAAGTGG|ATGATGCGAA|ATACGGCTTC|1740|
|GTCGCCTCTG|GCACGCTGAA|CCCGCAAAAA|GCGCGCGTTC|TGCTGCAACT|GGCTCTGACG|1800|
|CAAACCAAAG|ATCCGCAGCA|GATCCAGCAG|ATCTTCAATC|AGTACTAA| |1848|